(12) United States Patent
Genova et al.

(10) Patent No.: US 8,028,388 B2
(45) Date of Patent: Oct. 4, 2011

(54) SYSTEM FOR CUTTING A SUTURE TO CREATE TISSUE RETAINERS OF A DESIRED SHAPE AND SIZE

(75) Inventors: Perry Genova, Chapel Hill, NC (US); Robert C. Williams, III, Raleigh, NC (US); Warren Jewett, Cary, NC (US)

(73) Assignee: Quill Medical, Inc.

( * ) Notice: Subject to any disclaimer, the term of this patent is extended or adjusted under 35 U.S.C. 154(b) by 0 days.

(21) Appl. No.: 12/850,480

(22) Filed: Aug. 4, 2010

(65) Prior Publication Data

US 2010/0313723 A1  Dec. 16, 2010

Related U.S. Application Data

(63) Continuation of application No. 11/691,845, filed on Mar. 27, 2007, now Pat. No. 7,913,365, which is a continuation of application No. 10/486,123, filed as application No. PCT/US2002/027525 on Aug. 29, 2002, now Pat. No. 7,225,512, and a continuation-in-part of application No. 09/943,733, filed on Aug. 31, 2001, now Pat. No. 6,848,152.

(51) Int. Cl.
*B21F 25/00* (2006.01)
*B26D 7/01* (2006.01)

(52) U.S. Cl. .............................. 29/7.1; 83/78

(58) Field of Classification Search ............ 29/7.1, 29/7.2, 7.3, 50–56; 606/228, 215, 224, 216; 83/651, 78; 33/21.1
See application file for complete search history.

(56) References Cited

U.S. PATENT DOCUMENTS

| | | | |
|---|---|---|---|
| 709,392 A | 9/1902 | Brown |
| 733,723 A | 7/1903 | Lukens |
| 789,401 A | 5/1905 | Acheson |
| 816,026 A | 3/1906 | Meier |
| 879,758 A | 2/1908 | Foster |
| 1,142,510 A | 6/1915 | Engle |
| 1,248,825 A | 12/1917 | Dederer |
| 1,321,011 A | 11/1919 | Cottes |
| 1,558,037 A | 10/1925 | Morton |
| 1,728,316 A | 9/1929 | Wachenfeldt |
| 1,886,721 A | 11/1932 | O'Brien |

(Continued)

FOREIGN PATENT DOCUMENTS

BE  1014364  9/2003

(Continued)

OTHER PUBLICATIONS

International Search Report for PCT/US2007/074658 dated Jun. 12, 2007, 3 pages.

(Continued)

*Primary Examiner* — John C Hong
(74) *Attorney, Agent, or Firm* — Angiotech

(57) ABSTRACT

A system for manufacturing self-retaining suture is disclosed. The system includes a cutting bed for creating and supporting a suture during cutting of tissue-grasping elements at different angular positions. A cutting device is moved through the suture thread along a path which can include longitudinal, transverse, oscillating and depth components to create a desired tissue-grasping element on the surface of the suture. The path of the cutting device and the rotation of the suture relative to the cutting device are controlled so that a plurality of angularly-displaced tissue-grasping elements can be created on the suture.

20 Claims, 23 Drawing Sheets

U.S. PATENT DOCUMENTS

| | | |
|---|---|---|
| 2,094,578 A | 10/1937 | Blumenthal |
| 2,201,610 A | 5/1940 | Dawson, Jr. |
| 2,232,142 A | 2/1941 | Schumann |
| 2,254,620 A | 9/1941 | Miller |
| 2,347,956 A * | 5/1944 | Lansing .................. 30/90.6 |
| 2,355,907 A | 8/1944 | Cox |
| 2,421,193 A | 5/1947 | Gardner |
| 2,472,009 A | 5/1949 | Gardner |
| 2,572,936 A | 10/1951 | Kulp |
| 2,684,070 A | 7/1954 | Kelsey |
| 2,779,083 A | 1/1957 | Eaton |
| 2,814,296 A | 11/1957 | Everett |
| 2,817,339 A | 12/1957 | Sullivan |
| 2,866,256 A | 12/1958 | Matlin |
| 2,910,067 A | 10/1959 | White |
| 2,988,028 A | 6/1961 | Alcamo |
| 3,003,155 A | 10/1961 | Mielzynski |
| 3,068,869 A | 12/1962 | Shelden |
| 3,068,870 A | 12/1962 | Levin |
| 3,123,077 A | 3/1964 | Alcamo |
| 3,166,072 A | 1/1965 | Sullivan |
| 3,187,752 A | 6/1965 | Glick |
| 3,206,018 A | 9/1965 | Lewis |
| 3,209,652 A | 10/1965 | Burgsmueller |
| 3,209,754 A | 10/1965 | Brown |
| 3,214,810 A | 11/1965 | Mathison |
| 3,221,746 A | 12/1965 | Noble |
| 3,234,636 A | 2/1966 | Brown |
| 3,273,562 A | 9/1966 | Brown |
| 3,352,191 A | 11/1967 | Crawford |
| 3,378,010 A | 4/1968 | Codling |
| 3,385,299 A | 5/1968 | Le Roy |
| 3,494,006 A | 2/1970 | Brumlik |
| 3,525,340 A | 8/1970 | Gilbert |
| 3,527,223 A | 9/1970 | Shein |
| 3,545,608 A | 12/1970 | Berger |
| 3,570,497 A | 3/1971 | Lemole |
| 3,586,002 A | 6/1971 | Wood |
| 3,608,095 A | 9/1971 | Barry |
| 3,608,539 A | 9/1971 | Miller |
| 3,646,615 A | 3/1972 | Ness |
| 3,683,926 A | 8/1972 | Suzuki |
| 3,700,433 A | 10/1972 | Duhl |
| 3,716,058 A | 2/1973 | Tanner, Jr. |
| 3,720,055 A | 3/1973 | deMestral |
| 3,825,010 A | 7/1974 | McDonald |
| 3,833,972 A | 9/1974 | Brumlik |
| 3,845,641 A | 11/1974 | Waller |
| 3,847,156 A | 11/1974 | Trumble |
| 3,918,455 A | 11/1975 | Coplan |
| 3,951,261 A | 4/1976 | Mandel |
| 3,981,051 A | 9/1976 | Brumlik |
| 3,981,307 A | 9/1976 | Borysko |
| 3,985,138 A | 10/1976 | Jarvik |
| 3,985,227 A | 10/1976 | Thyen |
| 4,006,747 A | 2/1977 | Kronenthal |
| 4,008,303 A | 2/1977 | Glick |
| 4,027,608 A | 6/1977 | Arbuckle |
| 4,043,344 A | 8/1977 | Landi |
| D246,911 S | 1/1978 | Bess, Jr. |
| 4,069,825 A | 1/1978 | Akiyama |
| 4,073,298 A | 2/1978 | Le Roy |
| 4,137,921 A | 2/1979 | Okuzumi |
| 4,198,734 A | 4/1980 | Brumlik |
| 4,204,541 A | 5/1980 | Kapitanov |
| 4,204,542 A | 5/1980 | Bokros |
| 4,259,959 A | 4/1981 | Walker |
| 4,300,424 A | 11/1981 | Flinn |
| 4,311,002 A | 1/1982 | Dipalma |
| 4,313,448 A | 2/1982 | Stokes |
| 4,316,469 A | 2/1982 | Kapitanov |
| 4,317,451 A | 3/1982 | Cerwin |
| 4,428,376 A | 1/1984 | Mericle |
| 4,430,998 A | 2/1984 | Harvey |
| 4,434,796 A | 3/1984 | Karapetian |
| 4,454,875 A | 6/1984 | Pratt |
| 4,467,805 A | 8/1984 | Fukuda |
| 4,492,075 A | 1/1985 | Faure |
| 4,493,323 A | 1/1985 | Albright |
| 4,505,274 A | 3/1985 | Speelman |
| 4,510,934 A | 4/1985 | Batra |
| 4,531,522 A | 7/1985 | Bedi |
| 4,532,926 A | 8/1985 | O'Holla |
| 4,535,772 A | 8/1985 | Sheehan |
| 4,548,202 A | 10/1985 | Duncan |
| 4,553,544 A | 11/1985 | Nomoto |
| 4,610,250 A | 9/1986 | Green |
| 4,610,251 A | 9/1986 | Kumar |
| 4,635,637 A | 1/1987 | Schreiber |
| 4,637,380 A | 1/1987 | Orejola |
| 4,653,486 A | 3/1987 | Coker |
| 4,669,473 A | 6/1987 | Richards |
| 4,676,245 A | 6/1987 | Fukuda |
| 4,719,917 A | 1/1988 | Barrows |
| 4,741,330 A | 5/1988 | Hayhurst |
| 4,750,910 A | 6/1988 | Takayanagi |
| 4,751,621 A | 6/1988 | Jenkins |
| 4,776,337 A | 10/1988 | Palmaz |
| 4,832,025 A | 5/1989 | Coates |
| 4,841,960 A | 6/1989 | Garner |
| 4,865,026 A | 9/1989 | Barrett |
| 4,873,976 A | 10/1989 | Schreiber |
| 4,887,601 A | 12/1989 | Richards |
| 4,895,148 A | 1/1990 | Bays |
| 4,898,156 A | 2/1990 | Gatturna |
| 4,899,743 A | 2/1990 | Nicholson |
| 4,900,605 A | 2/1990 | Thorgersen |
| 4,905,367 A | 3/1990 | Pinchuk |
| 4,930,945 A | 6/1990 | Arai |
| 4,932,962 A | 6/1990 | Yoon |
| 4,946,468 A | 8/1990 | Li |
| 4,948,444 A | 8/1990 | Schutz |
| 4,950,258 A | 8/1990 | Kawai |
| 4,950,285 A | 8/1990 | Wilk |
| 4,968,315 A | 11/1990 | Gatturna |
| 4,976,715 A | 12/1990 | Bays |
| 4,981,149 A | 1/1991 | Yoon |
| 4,994,073 A | 2/1991 | Green |
| 4,997,439 A | 3/1991 | Chen |
| 5,002,550 A | 3/1991 | Li |
| 5,002,562 A | 3/1991 | Oberlander |
| 5,007,921 A | 4/1991 | Brown |
| 5,007,922 A | 4/1991 | Chen |
| 5,026,390 A | 6/1991 | Brown |
| 5,037,422 A | 8/1991 | Hayhurst |
| 5,041,129 A | 8/1991 | Hayhurst |
| 5,046,513 A | 9/1991 | Gatturna |
| 5,047,047 A | 9/1991 | Yoon |
| 5,053,047 A | 10/1991 | Yoon |
| 5,084,063 A | 1/1992 | Korthoff |
| 5,089,010 A | 2/1992 | Korthoff |
| 5,101,968 A | 4/1992 | Henderson |
| 5,102,418 A | 4/1992 | Granger |
| 5,102,421 A | 4/1992 | Anspach, Jr. |
| 5,103,073 A | 4/1992 | Danilov |
| 5,112,344 A | 5/1992 | Petros |
| 5,123,911 A | 6/1992 | Granger |
| 5,123,913 A | 6/1992 | Wilk |
| 5,123,919 A | 6/1992 | Sauter |
| 5,127,413 A | 7/1992 | Ebert |
| 5,133,738 A | 7/1992 | Korthoff |
| 5,141,520 A | 8/1992 | Goble |
| 5,147,382 A | 9/1992 | Gertzman |
| 5,156,788 A | 10/1992 | Chesterfield |
| 5,176,692 A | 1/1993 | Wilk |
| 5,179,964 A | 1/1993 | Cook |
| 5,192,274 A | 3/1993 | Bierman |
| 5,192,302 A | 3/1993 | Kensey |
| 5,192,303 A | 3/1993 | Gatturna |
| 5,197,597 A | 3/1993 | Leary |
| 5,207,679 A | 5/1993 | Li |
| 5,207,694 A | 5/1993 | Broome |
| 5,217,486 A | 6/1993 | Rice |
| 5,217,494 A | 6/1993 | Coggins |
| 5,222,508 A | 6/1993 | Contarini |
| 5,222,976 A | 6/1993 | Yoon |
| 5,224,946 A | 7/1993 | Hayhurst |

| | | | | | |
|---|---|---|---|---|---|
| 5,242,457 A | 9/1993 | Akopov | 5,702,462 A | 12/1997 | Oberlander |
| 5,246,441 A | 9/1993 | Ross | 5,709,692 A | 1/1998 | Mollenauer |
| 5,249,673 A | 10/1993 | Sinn | 5,716,358 A | 2/1998 | Ochoa |
| 5,258,013 A | 11/1993 | Granger | 5,716,376 A | 2/1998 | Roby |
| 5,263,973 A | 11/1993 | Cook | 5,722,991 A | 3/1998 | Colligan |
| 5,269,783 A | 12/1993 | Sander | 5,723,008 A | 3/1998 | Gordon |
| 5,282,832 A | 2/1994 | Toso | 5,725,557 A | 3/1998 | Gatturna |
| 5,292,326 A | 3/1994 | Green | 5,728,114 A | 3/1998 | Evans |
| 5,306,288 A | 4/1994 | Granger | 5,741,277 A | 4/1998 | Gordon |
| 5,306,290 A | 4/1994 | Martins | 5,763,411 A | 6/1998 | Edwardson |
| 5,320,629 A | 6/1994 | Noda | 5,765,560 A | 6/1998 | Verkerke |
| 5,330,488 A | 7/1994 | Goldrath | 5,779,719 A | 7/1998 | Klein |
| 5,330,503 A | 7/1994 | Yoon | 5,782,864 A | 7/1998 | Lizardi |
| 5,336,239 A | 8/1994 | Gimpelson | 5,807,403 A | 9/1998 | Beyar |
| 5,341,922 A | 8/1994 | Cerwin | 5,807,406 A | 9/1998 | Brauker |
| 5,342,376 A | 8/1994 | Ruff | 5,810,853 A | 9/1998 | Yoon |
| 5,342,395 A | 8/1994 | Jarrett | 5,814,051 A | 9/1998 | Wenstrom, Jr. |
| 5,352,515 A | 10/1994 | Jarrett | 5,843,087 A | 12/1998 | Jensen |
| 5,354,271 A | 10/1994 | Voda | 5,843,178 A | 12/1998 | Vanney |
| 5,354,298 A | 10/1994 | Lee | 5,863,360 A | 1/1999 | Wood |
| 5,358,511 A | 10/1994 | Gatturna | 5,884,859 A | 3/1999 | Ma |
| 5,372,146 A | 12/1994 | Branch | 5,887,594 A | 3/1999 | LoCicero, III |
| 5,374,268 A | 12/1994 | Sander | 5,891,166 A | 4/1999 | Schervinsky |
| 5,374,278 A | 12/1994 | Chesterfield | 5,893,856 A | 4/1999 | Jacob |
| 5,380,334 A | 1/1995 | Torrie | 5,895,395 A | 4/1999 | Yeung |
| 5,391,173 A | 2/1995 | Wilk | 5,895,413 A | 4/1999 | Nordstrom |
| 5,395,126 A | 3/1995 | Tresslar | 5,897,572 A | 4/1999 | Schulsinger |
| 5,403,346 A | 4/1995 | Loeser | 5,899,911 A | 5/1999 | Carter |
| 5,411,523 A | 5/1995 | Goble | 5,916,224 A | 6/1999 | Esplin |
| 5,414,988 A | 5/1995 | DiPalma | 5,919,234 A | 7/1999 | Lemperle |
| 5,417,691 A | 5/1995 | Hayhurst | 5,921,982 A | 7/1999 | Lesh |
| 5,425,746 A | 6/1995 | Proto | 5,925,078 A | 7/1999 | Anderson |
| 5,425,747 A | 6/1995 | Brotz | 5,931,855 A | 8/1999 | Buncke |
| 5,437,680 A | 8/1995 | Yoon | 5,935,138 A | 8/1999 | McJames, II |
| 5,450,860 A | 9/1995 | O'Connor | 5,938,668 A | 8/1999 | Scirica |
| 5,451,461 A | 9/1995 | Broyer | 5,950,633 A | 9/1999 | Lynch |
| 5,462,561 A | 10/1995 | Voda | 5,954,747 A | 9/1999 | Clark |
| 5,464,427 A | 11/1995 | Curtis | 5,968,097 A | 10/1999 | Frechet |
| 5,472,452 A | 12/1995 | Trott | 5,972,024 A | 10/1999 | Northrup, III |
| 5,478,353 A | 12/1995 | Yoon | 5,984,933 A | 11/1999 | Yoon |
| 5,480,403 A | 1/1996 | Lee | 5,993,459 A | 11/1999 | Larsen |
| 5,480,411 A | 1/1996 | Liu | 6,001,111 A | 12/1999 | Sepetka |
| 5,484,451 A | 1/1996 | Akopov | 6,012,216 A | 1/2000 | Esteves |
| 5,486,197 A | 1/1996 | Le | 6,015,410 A | 1/2000 | Tormala |
| 5,494,154 A | 2/1996 | Ainsworth | 6,024,757 A | 2/2000 | Hasse |
| 5,500,000 A | 3/1996 | Feagin | 6,027,523 A | 2/2000 | Schmieding |
| 5,500,991 A | 3/1996 | Demarest | 6,039,741 A | 3/2000 | Meislin |
| 5,520,084 A | 5/1996 | Chesterfield | 6,056,778 A | 5/2000 | Grafton |
| 5,520,691 A | 5/1996 | Branch | 6,063,105 A | 5/2000 | Totakura |
| 5,522,845 A | 6/1996 | Wenstrom, Jr. | 6,074,419 A | 6/2000 | Healy |
| 5,531,760 A | 7/1996 | Alwafaie | 6,076,255 A | 6/2000 | Shikakubo |
| 5,531,761 A | 7/1996 | Yoon | 6,083,244 A | 7/2000 | Lubbers |
| 5,531,790 A | 7/1996 | Frechet | 6,102,947 A | 8/2000 | Gordon |
| 5,533,982 A | 7/1996 | Rizk | 6,106,544 A | 8/2000 | Brazeau |
| 5,536,582 A | 7/1996 | Prasad | D433,753 S | 11/2000 | Weiss |
| 5,540,705 A | 7/1996 | Meade | 6,146,406 A | 11/2000 | Shluzas |
| 5,540,718 A | 7/1996 | Bartlett | 6,146,407 A | 11/2000 | Krebs |
| 5,546,957 A | 8/1996 | Heske | 6,149,660 A | 11/2000 | Laufer |
| 5,554,171 A | 9/1996 | Gatturna | 6,163,948 A | 12/2000 | Esteves |
| 5,566,822 A | 10/1996 | Scanlon | 6,165,203 A | 12/2000 | Krebs |
| 5,571,175 A | 11/1996 | Vanney | 6,168,633 B1 | 1/2001 | Shoher |
| 5,571,216 A | 11/1996 | Anderson | 6,174,324 B1 | 1/2001 | Egan |
| 5,573,543 A | 11/1996 | Akopov | 6,183,499 B1 | 2/2001 | Fischer |
| 5,584,859 A | 12/1996 | Brotz | 6,187,095 B1 | 2/2001 | Labrecque |
| 5,601,557 A | 2/1997 | Hayhurst | 6,206,908 B1 | 3/2001 | Roby |
| 5,626,590 A | 5/1997 | Wilk | 6,235,869 B1 | 5/2001 | Roby |
| 5,632,753 A | 5/1997 | Loeser | 6,241,747 B1 | 6/2001 | Ruff |
| 5,643,288 A | 7/1997 | Thompson | 6,251,143 B1 | 6/2001 | Schwartz |
| 5,643,295 A | 7/1997 | Yoon | 6,264,675 B1 | 7/2001 | Brotz |
| 5,643,319 A | 7/1997 | Green | 6,267,772 B1 | 7/2001 | Mulhauser |
| 5,647,874 A | 7/1997 | Hayhurst | 6,270,517 B1 | 8/2001 | Brotz |
| 5,649,939 A | 7/1997 | Reddick | 6,315,788 B1 | 11/2001 | Roby |
| 5,653,716 A | 8/1997 | Malo | 6,319,231 B1 | 11/2001 | Andrulitis |
| 5,662,714 A | 9/1997 | Charvin | 6,334,865 B1 | 1/2002 | Redmond |
| 5,669,935 A | 9/1997 | Rosenman | 6,387,363 B1 | 5/2002 | Gruskin |
| D386,583 S | 11/1997 | Ferragamo | 6,388,043 B1 | 5/2002 | Langer |
| 5,683,417 A | 11/1997 | Cooper | 6,395,029 B1 | 5/2002 | Levy |
| D387,161 S | 12/1997 | Ferragamo | D462,766 S | 9/2002 | Jacobs |
| 5,697,976 A | 12/1997 | Chesterfield | 6,443,962 B1 | 9/2002 | Gaber |

| | | |
|---|---|---|
| 6,463,719 B2 | 10/2002 | Dey |
| 6,471,715 B1 | 10/2002 | Weiss |
| 6,478,809 B1 | 11/2002 | Brotz |
| 6,485,503 B2 | 11/2002 | Jacobs |
| 6,491,701 B2 | 12/2002 | Tierney |
| 6,494,898 B1 | 12/2002 | Roby |
| 6,495,127 B1 | 12/2002 | Wallace |
| RE37,963 E | 1/2003 | Thal |
| 6,506,190 B1 | 1/2003 | Walshe |
| 6,511,488 B1 | 1/2003 | Marshall |
| 6,514,265 B2 | 2/2003 | Ho |
| 6,527,795 B1 | 3/2003 | Lizardi |
| 6,551,343 B1 | 4/2003 | Tormala |
| 6,554,802 B1 | 4/2003 | Pearson |
| 6,565,597 B1 | 5/2003 | Fearnot |
| 6,592,609 B1 | 7/2003 | Bonutti |
| 6,596,296 B1 | 7/2003 | Nelson |
| 6,599,310 B2 | 7/2003 | Leung |
| 6,607,541 B1 | 8/2003 | Gardiner |
| 6,610,078 B1 | 8/2003 | Bru-Magniez |
| 6,613,059 B2 | 9/2003 | Schaller |
| 6,613,254 B1 | 9/2003 | Shiffer |
| 6,616,982 B2 | 9/2003 | Merrill |
| 6,623,492 B1 | 9/2003 | Berube |
| 6,626,930 B1 | 9/2003 | Allen |
| 6,641,592 B1 | 11/2003 | Sauer |
| 6,641,593 B1 | 11/2003 | Schaller |
| 6,645,226 B1 | 11/2003 | Jacobs |
| 6,645,227 B2 | 11/2003 | Fallin |
| 6,648,921 B2 | 11/2003 | Anderson |
| 6,656,182 B1 | 12/2003 | Hayhurst |
| 6,689,153 B1 | 2/2004 | Skiba |
| 6,702,844 B1 | 3/2004 | Lazarus |
| 6,712,830 B2 | 3/2004 | Esplin |
| 6,716,234 B2 | 4/2004 | Grafton |
| 6,720,402 B2 | 4/2004 | Langer |
| 6,726,705 B2 | 4/2004 | Peterson |
| 6,746,443 B1 | 6/2004 | Morley |
| 6,746,458 B1 | 6/2004 | Cloud |
| 6,749,616 B1 | 6/2004 | Nath |
| 6,773,450 B2 | 8/2004 | Leung |
| 6,783,554 B2 | 8/2004 | Amara |
| 6,814,748 B1 | 11/2004 | Baker |
| 6,818,010 B2 | 11/2004 | Eichhorn |
| 6,838,493 B2 | 1/2005 | Williams |
| 6,848,152 B2 | 2/2005 | Genova |
| 6,852,825 B2 | 2/2005 | Lendlein |
| 6,858,222 B2 | 2/2005 | Nelson |
| 6,860,891 B2 | 3/2005 | Schulze |
| 6,860,901 B1 | 3/2005 | Baker |
| 6,877,934 B2 | 4/2005 | Gainer |
| 6,881,766 B2 | 4/2005 | Hain |
| 6,893,452 B2 | 5/2005 | Jacobs |
| 6,905,484 B2 | 6/2005 | Buckman |
| 6,911,035 B1 | 6/2005 | Blomme |
| 6,911,037 B2 | 6/2005 | Gainor |
| 6,913,607 B2 | 7/2005 | Ainsworth |
| 6,921,811 B2 | 7/2005 | Zamora |
| 6,923,819 B2 | 8/2005 | Meade |
| 6,945,980 B2 | 9/2005 | Nguyen |
| 6,960,221 B2 | 11/2005 | Ho |
| 6,960,233 B1 | 11/2005 | Berg |
| 6,974,450 B2 | 12/2005 | Weber |
| 6,981,983 B1 | 1/2006 | Rosenblatt |
| 6,984,241 B2 | 1/2006 | Lubbers |
| 6,986,780 B2 | 1/2006 | Rudnick |
| 6,991,643 B2 | 1/2006 | Saadat |
| 6,996,880 B2 | 2/2006 | Kurtz, Jr. |
| 7,021,316 B2 | 4/2006 | Leiboff |
| 7,033,379 B2 | 4/2006 | Peterson |
| 7,033,603 B2 | 4/2006 | Nelson |
| 7,037,984 B2 | 5/2006 | Lendlein |
| 7,048,748 B1 | 5/2006 | Ustuner |
| 7,056,331 B2 | 6/2006 | Kaplan |
| 7,056,333 B2 | 6/2006 | Walshe |
| 7,057,135 B2 | 6/2006 | Li |
| 7,070,610 B2 | 7/2006 | Im |
| 7,081,135 B2 | 7/2006 | Smith |
| 7,083,637 B1 | 8/2006 | Tannhauser |
| 7,083,648 B2 | 8/2006 | Yu |
| 7,107,090 B2 | 9/2006 | Salisbury, Jr. |
| 7,112,214 B2 | 9/2006 | Peterson |
| 7,125,403 B2 | 10/2006 | Julian |
| 7,125,413 B2 | 10/2006 | Grigoryants |
| D532,107 S | 11/2006 | Peterson |
| 7,138,441 B1 | 11/2006 | Zhang |
| 7,141,302 B2 | 11/2006 | Mueller |
| 7,144,401 B2 | 12/2006 | Yamamoto |
| 7,144,412 B2 | 12/2006 | Wolf |
| 7,144,415 B2 | 12/2006 | Del Rio |
| 7,150,757 B2 | 12/2006 | Fallin |
| 7,156,858 B2 | 1/2007 | Schuldt-Hempe |
| 7,156,862 B2 | 1/2007 | Jacobs |
| 7,160,312 B2 | 1/2007 | Saadat |
| 7,166,570 B2 | 1/2007 | Hunter |
| 7,172,595 B1 | 2/2007 | Goble |
| 7,172,615 B2 | 2/2007 | Morriss |
| 7,186,262 B2 | 3/2007 | Saadat |
| 7,195,634 B2 | 3/2007 | Schmieding |
| 7,211,088 B2 | 5/2007 | Grafton |
| 7,214,230 B2 | 5/2007 | Brock |
| 7,217,744 B2 | 5/2007 | Lendlein |
| 7,225,512 B2 | 6/2007 | Genova |
| 7,226,468 B2 | 6/2007 | Ruff |
| 7,232,447 B2 | 6/2007 | Gellman |
| 7,244,270 B2 | 7/2007 | Lesh |
| 7,279,612 B1 | 10/2007 | Heaton |
| 7,297,142 B2 | 11/2007 | Brock |
| 7,322,105 B2 | 1/2008 | Lewis |
| 7,371,253 B2 | 5/2008 | Leung |
| 7,513,904 B2 | 4/2009 | Sulamanidze |
| 7,514,095 B2 | 4/2009 | Nelson |
| 7,582,105 B2 | 9/2009 | Kolster |
| 7,601,164 B2 | 10/2009 | Wu |
| 7,624,487 B2 | 12/2009 | Trull |
| 2001/0011187 A1 | 8/2001 | Pavcnik |
| 2001/0018599 A1 | 8/2001 | D'Aversa |
| 2001/0039450 A1 | 11/2001 | Pavcnik |
| 2001/0044637 A1 | 11/2001 | Jacobs |
| 2001/0051807 A1 | 12/2001 | Grafton |
| 2001/0051815 A1 | 12/2001 | Esplin |
| 2002/0007218 A1 | 1/2002 | Cauthen |
| 2002/0022861 A1 | 2/2002 | Jacobs |
| 2002/0029066 A1 | 3/2002 | Foerster |
| 2002/0069617 A1 | 6/2002 | Dey |
| 2002/0077448 A1 | 6/2002 | Antal |
| 2002/0077631 A1 | 6/2002 | Lubbers |
| 2002/0095164 A1 | 7/2002 | Andreas |
| 2002/0099394 A1 | 7/2002 | Houser |
| 2002/0111641 A1 | 8/2002 | Peterson |
| 2002/0111688 A1 | 8/2002 | Cauthen |
| 2002/0138009 A1 | 9/2002 | Brockway |
| 2002/0151980 A1 | 10/2002 | Cauthen |
| 2002/0173807 A1 | 11/2002 | Jacobs |
| 2002/0173822 A1 | 11/2002 | Justin |
| 2002/0179718 A1 | 12/2002 | Murokh |
| 2003/0014077 A1 | 1/2003 | Leung |
| 2003/0040795 A1 | 2/2003 | Elson |
| 2003/0041426 A1 | 3/2003 | Genova |
| 2003/0065360 A1 | 4/2003 | Jacobs |
| 2003/0065402 A1 | 4/2003 | Anderson |
| 2003/0069602 A1 | 4/2003 | Jacobs |
| 2003/0074021 A1 | 4/2003 | Morriss |
| 2003/0074023 A1 | 4/2003 | Kaplan |
| 2003/0078604 A1 | 4/2003 | Walshe |
| 2003/0088270 A1 | 5/2003 | Lubbers |
| 2003/0097150 A1 | 5/2003 | Fallin |
| 2003/0105489 A1 | 6/2003 | Eichhorn |
| 2003/0149447 A1 | 8/2003 | Morency |
| 2003/0158604 A1 | 8/2003 | Cauthen, III |
| 2003/0167072 A1 | 9/2003 | Oberlander |
| 2003/0203003 A1 | 10/2003 | Nelson |
| 2003/0204195 A1 | 10/2003 | Keane |
| 2003/0229361 A1 | 12/2003 | Jackson |
| 2003/0236550 A1 | 12/2003 | Peterson |
| 2003/0236551 A1 | 12/2003 | Peterson |
| 2004/0010275 A1 | 1/2004 | Jacobs |
| 2004/0010276 A1 | 1/2004 | Jacobs |

| | | | | | | |
|---|---|---|---|---|---|---|
| 2004/0015187 A1 | 1/2004 | Lendlein | | 2006/0111742 A1 | 5/2006 | Kaplan |
| 2004/0024420 A1 | 2/2004 | Lubbers | | 2006/0122608 A1 | 6/2006 | Fallin |
| 2004/0028655 A1 | 2/2004 | Nelson | | 2006/0135994 A1 | 6/2006 | Ruff |
| 2004/0030354 A1 | 2/2004 | Leung | | 2006/0135995 A1 | 6/2006 | Ruff |
| 2004/0039415 A1 | 2/2004 | Zamierowski | | 2006/0142784 A1 | 6/2006 | Kontos |
| 2004/0059377 A1 | 3/2004 | Peterson | | 2006/0193769 A1 | 8/2006 | Nelson |
| 2004/0059378 A1 | 3/2004 | Peterson | | 2006/0194721 A1 | 8/2006 | Allen |
| 2004/0060409 A1 | 4/2004 | Leung | | 2006/0200062 A1 | 9/2006 | Saadat |
| 2004/0060410 A1 | 4/2004 | Leung | | 2006/0207612 A1 | 9/2006 | Jackson |
| 2004/0068293 A1 | 4/2004 | Scalzo | | 2006/0229671 A1 | 10/2006 | Steiner |
| 2004/0068294 A1 | 4/2004 | Scalzo | | 2006/0235445 A1 | 10/2006 | Birk |
| 2004/0088003 A1 | 5/2004 | Leung | | 2006/0235447 A1 | 10/2006 | Walshe |
| 2004/0093023 A1 | 5/2004 | Allen | | 2006/0235516 A1 | 10/2006 | Cavazzoni |
| 2004/0093028 A1 | 5/2004 | Ruff | | 2006/0241658 A1 | 10/2006 | Cerundolo |
| 2004/0098051 A1 | 5/2004 | Fallin | | 2006/0249405 A1 | 11/2006 | Cerwin |
| 2004/0106949 A1 | 6/2004 | Cohn | | 2006/0253126 A1 | 11/2006 | Bjerken |
| 2004/0138683 A1 | 7/2004 | Shelton | | 2006/0257629 A1 | 11/2006 | Lendlein |
| 2004/0153153 A1 | 8/2004 | Elson | | 2006/0258938 A1 | 11/2006 | Hoffman |
| 2004/0167572 A1 | 8/2004 | Roth | | 2006/0272979 A1 | 12/2006 | Lubbers |
| 2004/0167575 A1 | 8/2004 | Roby | | 2006/0276808 A1 | 12/2006 | Arnal |
| 2004/0193191 A1 | 9/2004 | Starksen | | 2006/0282099 A1 | 12/2006 | Stokes |
| 2004/0193217 A1 | 9/2004 | Lubbers | | 2006/0286289 A1 | 12/2006 | Prajapati |
| 2004/0193257 A1 | 9/2004 | Wu | | 2006/0287675 A1 | 12/2006 | Prajapati |
| 2004/0226427 A1 | 11/2004 | Trull | | 2006/0287676 A1 | 12/2006 | Prajapati |
| 2004/0237736 A1 | 12/2004 | Genova | | 2006/0293710 A1 | 12/2006 | Foerster |
| 2004/0254609 A1 | 12/2004 | Esplin | | 2007/0005109 A1 | 1/2007 | Popadiuk |
| 2004/0260340 A1 | 12/2004 | Jacobs | | 2007/0005110 A1 | 1/2007 | Collier |
| 2004/0265282 A1 | 12/2004 | Wright | | 2007/0021779 A1 | 1/2007 | Garvin |
| 2004/0267309 A1 | 12/2004 | Garvin | | 2007/0027475 A1 | 2/2007 | Pagedas |
| 2005/0004601 A1 | 1/2005 | Kong | | 2007/0038249 A1 | 2/2007 | Kolster |
| 2005/0004602 A1 | 1/2005 | Hart | | 2007/0065663 A1 | 3/2007 | Trull |
| 2005/0033324 A1 | 2/2005 | Phan | | 2007/0088391 A1 | 4/2007 | McAlexander |
| 2005/0033367 A1 | 2/2005 | Leung | | 2007/0135840 A1 | 6/2007 | Schmieding |
| 2005/0034431 A1 | 2/2005 | Dey | | 2007/0135843 A1 | 6/2007 | Burkhart |
| 2005/0059984 A1 | 3/2005 | Chanduszko | | 2007/0151961 A1 | 7/2007 | Kleine |
| 2005/0065533 A1 | 3/2005 | Magen | | 2007/0156175 A1 | 7/2007 | Weadock |
| 2005/0070959 A1 | 3/2005 | Cichocki, Jr. | | 2007/0167958 A1 | 7/2007 | Sulamanidze |
| 2005/0080455 A1 | 4/2005 | Schmieding | | 2007/0187861 A1 | 8/2007 | Genova |
| 2005/0085857 A1 | 4/2005 | Peterson | | 2007/0208355 A1 | 9/2007 | Ruff |
| 2005/0096698 A1 | 5/2005 | Lederman | | 2007/0208377 A1 | 9/2007 | Kaplan |
| 2005/0106211 A1 | 5/2005 | Nelson | | 2007/0219587 A1 | 9/2007 | Accardo |
| 2005/0113936 A1 | 5/2005 | Brustad | | 2007/0224237 A1 | 9/2007 | Hwang |
| 2005/0119694 A1 | 6/2005 | Jacobs | | 2007/0225642 A1 | 9/2007 | Houser |
| 2005/0125020 A1 | 6/2005 | Meade | | 2007/0225761 A1 | 9/2007 | Shetty |
| 2005/0125034 A1 | 6/2005 | Cichocki, Jr. | | 2007/0227914 A1 | 10/2007 | Cerwin |
| 2005/0125035 A1 | 6/2005 | Cichocki, Jr. | | 2007/0233188 A1 | 10/2007 | Hunt |
| 2005/0149064 A1 | 7/2005 | Peterson | | 2007/0239206 A1 | 10/2007 | Shelton, IV |
| 2005/0149118 A1 | 7/2005 | Koyfman | | 2007/0257395 A1 | 11/2007 | Lindh |
| 2005/0154255 A1 | 7/2005 | Jacobs | | 2007/0282247 A1 | 12/2007 | Desai |
| 2005/0171561 A1 | 8/2005 | Songer | | 2008/0004603 A1 | 1/2008 | Larkin |
| 2005/0177190 A1 | 8/2005 | Zamierowski | | 2008/0009838 A1 | 1/2008 | Schena |
| 2005/0182444 A1 | 8/2005 | Peterson | | 2008/0009888 A1 | 1/2008 | Ewers |
| 2005/0182445 A1 | 8/2005 | Zamierowski | | 2008/0009902 A1 | 1/2008 | Hunter |
| 2005/0197699 A1 | 9/2005 | Jacobs | | 2008/0027273 A1 | 1/2008 | Gutterman |
| 2005/0199249 A1 | 9/2005 | Karram | | 2008/0027486 A1 | 1/2008 | Jones |
| 2005/0203576 A1 | 9/2005 | Sulamanidze | | 2008/0046094 A1 | 2/2008 | Han |
| 2005/0209542 A1 | 9/2005 | Jacobs | | 2008/0058869 A1 | 3/2008 | Stopek |
| 2005/0209612 A1 | 9/2005 | Nakao | | 2008/0066764 A1 | 3/2008 | Paraschac |
| 2005/0234510 A1 | 10/2005 | Zamierowski | | 2008/0066765 A1 | 3/2008 | Paraschac |
| 2005/0240220 A1 | 10/2005 | Zamierowski | | 2008/0066766 A1 | 3/2008 | Paraschac |
| 2005/0240224 A1 | 10/2005 | Wu | | 2008/0066767 A1 | 3/2008 | Paraschac |
| 2005/0267531 A1 | 12/2005 | Ruff | | 2008/0077181 A1 | 3/2008 | Jones |
| 2005/0267532 A1 | 12/2005 | Wu | | 2008/0082113 A1 | 4/2008 | Bishop |
| 2005/0277984 A1 | 12/2005 | Long | | 2008/0082129 A1 | 4/2008 | Jones |
| 2005/0283246 A1 | 12/2005 | Cauthen | | 2008/0086169 A1 | 4/2008 | Jones |
| 2006/0020272 A1 | 1/2006 | Gildenberg | | 2008/0086170 A1 | 4/2008 | Jones |
| 2006/0030884 A1 | 2/2006 | Yeung | | 2008/0109036 A1 | 5/2008 | Stopek |
| 2006/0036266 A1 | 2/2006 | Sulamanidze | | 2008/0132943 A1 | 6/2008 | Maiorino |
| 2006/0058574 A1 | 3/2006 | Priewe | | 2008/0195147 A1 | 8/2008 | Stopek |
| 2006/0058799 A1 | 3/2006 | Elson | | 2008/0208358 A1 | 8/2008 | Bellamkonda |
| 2006/0058844 A1 | 3/2006 | White | | 2008/0215072 A1 | 9/2008 | Kelly |
| 2006/0064115 A1 | 3/2006 | Allen | | 2008/0221618 A1 | 9/2008 | Chen |
| 2006/0064116 A1 | 3/2006 | Allen | | 2008/0234731 A1 | 9/2008 | Leung |
| 2006/0064127 A1 | 3/2006 | Fallin | | 2008/0248216 A1 | 10/2008 | Yeung |
| 2006/0079935 A1 | 4/2006 | Kolster | | 2008/0262542 A1 | 10/2008 | Sulamanidze |
| 2006/0085016 A1 | 4/2006 | Eremia | | 2008/0281338 A1 | 11/2008 | Wohlert |
| 2006/0089525 A1 | 4/2006 | Mamo | | 2008/0312688 A1 | 12/2008 | Nawrocki |
| 2006/0089672 A1 | 4/2006 | Martinek | | 2009/0012560 A1 | 1/2009 | Hunter |
| 2006/0111734 A1 | 5/2006 | Kaplan | | 2009/0018577 A1 | 1/2009 | Leung |

| | | | |
|---|---|---|---|
| 2009/0043336 A1 | 2/2009 | Yuan |
| 2009/0076543 A1 | 3/2009 | Maiorino |
| 2009/0099597 A1 | 4/2009 | Isse |
| 2009/0107965 A1 | 4/2009 | D'Agostino |
| 2009/0112259 A1 | 4/2009 | D'Agostino |
| 2009/0200487 A1 | 8/2009 | Maiorino |
| 2009/0210006 A1 | 8/2009 | Cohen |
| 2009/0226500 A1 | 9/2009 | Avelar |
| 2009/0248066 A1 | 10/2009 | Wilkie |
| 2009/0248067 A1 | 10/2009 | Maiorino |
| 2009/0248070 A1 | 10/2009 | Kosa |
| 2009/0250356 A1 | 10/2009 | Kirsch |
| 2009/0259233 A1 | 10/2009 | Bogart |
| 2009/0259251 A1 | 10/2009 | Cohen |
| 2009/0287245 A1 | 11/2009 | Ostrovsky |
| 2009/0299407 A1 | 12/2009 | Yuan |
| 2009/0299408 A1 | 12/2009 | Schuldt-Hempe |
| 2009/0306710 A1 | 12/2009 | Lindh |
| 2010/0023055 A1 | 1/2010 | Rousseau |
| 2010/0057123 A1 | 3/2010 | D'Agostino |
| 2010/0063540 A1 | 3/2010 | Maiorino |
| 2010/0071833 A1 | 3/2010 | Maiorino |
| 2010/0087855 A1 | 4/2010 | Leung |
| 2010/0101707 A1 | 4/2010 | Maiorino |
| 2010/0140115 A1 | 6/2010 | Kirsch |
| 2010/0294103 A1 | 11/2010 | Genova |
| 2010/0294104 A1 | 11/2010 | Genova |
| 2010/0294105 A1 | 11/2010 | Genova |
| 2010/0294106 A1 | 11/2010 | Genova |
| 2010/0294107 A1 | 11/2010 | Genova |
| 2010/0313723 A1 | 12/2010 | Genova |
| 2010/0313729 A1 | 12/2010 | Genova |
| 2010/0313730 A1 | 12/2010 | Genova |

FOREIGN PATENT DOCUMENTS

| | | |
|---|---|---|
| CN | 2640420 | 9/2004 |
| DE | 1810800 | 6/1970 |
| DE | 3227984 | 7/1982 |
| DE | 4302895 | 8/1994 |
| DE | 19618891 | 4/1997 |
| DE | 19833703 | 2/2000 |
| DE | 102005004317 | 6/2006 |
| EP | 0329787 | 8/1989 |
| EP | 0428253 | 5/1991 |
| EP | 0576337 | 12/1993 |
| EP | 0632999 | 1/1995 |
| EP | 0612504 | 11/1997 |
| EP | 0826337 | 3/1998 |
| EP | 0839499 | 5/1998 |
| EP | 0913123 | 5/1999 |
| EP | 0960600 | 12/1999 |
| EP | 1075843 | 2/2001 |
| FR | 2619129 | 2/1989 |
| FR | 2693108 | 1/1994 |
| GB | 267007 | 3/1927 |
| GB | 1091282 | 11/1967 |
| GB | 1428560 | 3/1976 |
| GB | 1506362 | 4/1978 |
| JP | 354116419 | 9/1979 |
| JP | 63288146 | 11/1988 |
| JP | 01113091 | 5/1989 |
| JP | 11332828 | 12/1999 |
| KR | 6013299 A | 2/2006 |
| NZ | 501224 | 3/2002 |
| NZ | 531262 | 6/2002 |
| RU | 1745214 | 7/1992 |
| RU | 1752358 | 8/1992 |
| RU | 2139690 | 10/1999 |
| WO | WO9606565 | 3/1996 |
| WO | WO9852473 | 11/1998 |
| WO | WO9921488 | 5/1999 |
| WO | WO9905477 | 11/1999 |
| WO | WO0051658 | 9/2000 |
| WO | WO03001979 | 1/2003 |
| WO | WO03017850 | 3/2003 |
| WO | WO03045255 | 6/2003 |
| WO | WO03103733 | 12/2003 |
| WO | WO03103972 | 12/2003 |
| WO | WO2004014236 | 2/2004 |
| WO | WO2004030520 | 4/2004 |
| WO | WO2004030704 | 4/2004 |
| WO | WO2004030705 | 4/2004 |
| WO | WO2004112853 | 12/2004 |
| WO | WO2006005144 | 1/2006 |
| WO | WO2006061868 | 6/2006 |
| WO | WO2006082060 | 8/2006 |
| WO | WO2006099703 | 9/2006 |
| WO | WO2007053812 | 5/2007 |
| WO | WO2007133103 | 11/2007 |
| WO | WO2007145614 | 12/2007 |
| WO | WO2009068252 | 6/2009 |
| WO | WO2009087105 | 7/2009 |
| WO | WO2010052007 | 5/2010 |

OTHER PUBLICATIONS

International Search Report for PCT/US2008/060127 dated Sep. 23, 2008, 5 pages.

International Search Report for PCT/US2008/064921 dated Nov. 19, 2008, 3 pages.

International Search Report for PCT/US2008/075849 dated Mar. 18, 2009, 4 pages.

Singapore Search Report for Singapore Patent Application No. 200702625-5 dated Nov. 26, 2008, 7 pages.

Singapore Search Report for Singapore Patent Application No. 200702350-0 dated Nov. 26, 2008, 6 pages.

Singapore Search Report for Singapore Patent Application No. 200703688-2 dated Nov. 26, 2008, 7 pages.

European Search Report for EP07015905.8 dated Oct. 23, 2007, 2 pages.

European Search Report for EP10000629.5. dated Mar. 10, 2010, 4 pages.

European Search Report for EP10011871.0 dated Dec. 3, 2010, 2 pages.

European Search Report for EP10011868.6 dated Dec. 6, 2010, 2 pages.

European Search Report for EP10186592.1 dated Jan. 19, 2011, 2 pages.

Mason, M.L., "Primary and secondary tendon suture. A discussion of the significance of technique in tendon surgery", Surg Gynecol Obstet 70 (1940).

McKee, G.K., "Metal anastomosis tubes in tendon suture", The Lancet, May 26, 1945, 659-660.

Mansberger, et al., "A New Type Pull-Out Wire for Tendon Surgery: A Preliminary Report", Department of Surgery, University Hospital and University of Maryland School of Medicine, Baltimore, Maryland, Received for Publication May 10, 1951, pp. 119-121.

Jennings et al., "A new technique in primary tendon repair", Surg Gynecol Obstet Nov. 1952;95(5):597-600.

Bunnell, S., "Gig pull-out suture for tendons", J Bone Joint Surg Am. Jul. 1954;36-A(4):850-1.

Verdan, Claude, "Primary Repair of Flexor Tendons", Journal of Bone and Joint Surgery Jun. 1960; 42(4):647-657.

Potenza, Austin, "Tendon Healing Within the Flexor Digital Sheath in the Dog: An Experimental Study", Journal of Bone & Joint Surgery Jan. 1962; 44A(1):49-64.

Pulvertaft, "Suture Materials and Tendon Junctures", American Journal of Surgery Mar. 1965; 109:346-352.

Buncke, Jr., H.J. et al., "The suture repair of one-millimeter vessels, micro-vascular surgery", Report of First Conference; Oct. 6-7, 1966; pp. 24-35 (esp. p. 34), USA.

McKenzie, A.R., "An Experimental Multiple Barbed Suture for the Long Flexor Tendons of the Palm and Fingers", Journal of Bone and Joint Surgery 1967; 49B(3): 440-447.

Zoltan, Janos, "Cicatrix Optimia: Techniques for Ideal Wound Healing", English language edition University Park Press, Baltimore, 1977:Chapter 3; pp. 54-55.

Han, Hongtao et al., "Mating and Pricing Micromechanical Structures for Surface Bonding Applications", Proceedings of the 1991 Micro Electro Mechanical Systems (MEMS >91), An Investigation of Micro Structures, Sensors, Actuators, Machines and Robots, Feb. 1991, pp. 253-258.

Malina, Martin et al., "Endovascular AAA Exclusion: Will Stents With Hooks and Barbs Prevent Stent-Graft Migration", Journal Endovascular Surgery 1998(5): 310-317.

Boenisch, U.W. et al., "Pull-our strength and stiffness of meniscal repair using absorbable arrows or Ti-Cron vertical and horizontal loop sutures", American Journal of Sports Medicine, Sep.-Oct. 1999, pp. 626-631, vol. 27, Issue 5.

Sulamanidze, MD, M.A., et al., "Management of Facial Rhytids by Subcutaneous Soft Tissue Dissection", International Journal of Cosmetic Surgery and Aesthetic Dermatology, vol. 2(4), 2000, pp. 255-259.

Rofin-Baasel, "Laser Marking on Plastic Materials", 2001.RB50.0, Rofin-Baasel Inc. 2001, 2 pages.

Semenov, G. M. et al., "Surgical Suture", 2001, pp. 12-13 and 92-98, Piter, Saint Petersburg.

Sulamanidze, M.A. et al., "Facial lifting with Aptos threads", International Journal of Cosmetic Surgery and Aesthetic Dermatology, 2001, pp. 1-8, No. 4.

Dattillo, Jr., Philip Paul, "Medical Textile: Application of an Absorbable Barbed Bi-Directional Surgical Suture", Journal of Textile and Apparel, Technology and Management, vol. 2(2), Spring 2002, pp. 1-5.

Lendlein, Andreas et al., "Biodegradable, Elastic Shape-Memory Polymers for Potential Biomedical Applications", Science vol. 296; May 31, 2002, pp. 1673-1676.

Leung, J. et al., "Barbed, Bi-directional Medical Sutures: Biomechanical Properties and Wound Closure Efficacy Study", 2002 Society for Biomaterials 28$^{th}$ Annual Meeting Transactions, 1 page.

Sulamanidze, MD, M.A., et al., "Removal of Facial Soft Tissue Ptosis with Special Threads", Dermatol Surg 2002; 28; pp. 367-371.

Lendlein, Andreas et al., "Shape-Memory Polymers", Angew, Chem. Int. Ed. 2002, 41, 2034-2057.

Sulamanidze, MD, M.A., et al., "Clinical aspects of bloodless facelift using APTOS filaments", A.V. Vishnevsky Institute of Surgery, Bol= shaya Serpukhovskaya ul., 27, 113811 Moscow, Russia, (2002):24-34.

Sulamanidze, MD, M.A., et al., "Morphological foundations of facelift using APTOS filaments", Bolshaya Serpukhovskaya ul., 27, 113811 Moscow, Russia, (2002): 19-26.

Dattillo, Jr., Philip Paul, et al., "Tissue Holding Performance of Knotless Absorbable Sutures", 2003 Society for Biomaterials 29$^{th}$ Annual Meeting Transactions, p. 101.

Ingle, Nilesh P et al., "Mechanical Performance and Finite Element Analysis of Bi-directional Barbed Sutures", Master of Science in Textile Technology & Management at North Carolina State University Aug. 2003, 126 pages.

Kuniholm, Jonathan Fairbank, et al., "Automated Knot Tying for Fixation in Minimally Invasive, Robot Assisted Cardiac Surgery", Master of Science in Mechanical & Aerospace Engineering at North Carolina State University May 2003, 71 pages.

Leung, J. et al., "Barbed Bi-directional Surgical Sutures: In Vivo Strength and Histopathology Evaluations", 2003 Society for Biomaterials 29$^{th}$ Annual Meeting Transactions, p. 100.

Li, Yang Yang, et al., "Polymer Replicas of Photonic Porous Silicon for Sensing and Drug Delivery Applications", Science vol. 299; Mar. 28, 2003, pp. 2045-2047.

Leung, Jeffrey C. et al., "Barbed, Bi-Directional Surgical Sutures", International Conference & Exhibition on Healthcare & Medical Textiles, Jul. 8-9, 2003; 1-8.

Szarmach, Robin et al., "An Expanded Surgical Suture and Needle Evaulation and Selection Program By a Healthcare Resource Management Group Purchasing Organization", Journal of Long-Term Effects of Medical Implants 2003; 13(3); 155-170.

Ingle, Nilesh P et al., "Barbed Suture Anchoring Strength: Applicability to Dissimilar Polymeric Materials", College of Textiles, North Carolina State University, 7$^{th}$ World Biomaterials Congress 2004, 1 page.

Leung, J. et al., "Performance Enhancement of a Knotless Suture via Barb Geometry Modifications", 7$^{th}$ World Biomaterials Congress 2004, 1 page.

Wu, Woffles, "Barbed Sutures in Facial Rejuvenation", Aesthetic Surgery Journal 2004(24): 582-587.

Quill Medical, Inc., "Quill Medical's Novel-Self-Anchoring Surgical Suture Approved for Sale in Europe", Press Release; Research Triangle Park, N.C., May 10, 2004, 1 page.

Buckley, Patrick R., "Actuation of Shape Memory Polymer using Magnetic Fields for Applications in Medical Devices", Master of Science in Mechanical Engineering at the Massachusetts Institute of Technology Jun. 2003, 144 pgs.

Quill Medical, Inc., "Barbed sutures, wrinkle filters give patients more innovative, non-surgical options", Press Release of Program presented at American Society of Plastic Surgeons annual scientific meeting; Philadelphia, Oct. 9, 2004, 3 pages.

Leung, J. et al., "Barbed Suture Technology: Recent Advances", Medical Textiles 2004, Advances in Biomedical Textiles and Healthcare Products, Conference Proceedings, IFAI Expo 2004, Oct. 26-27, 2004, Pittsburgh, PA., pp. 62-80.

Quill Medical, Inc., "Quill Medical, Inc. Receives FDA Clearance for First-in-Class Knot-Less Self-Anchoring Surgical Suture", Press Release; Research Triangle Park, N.C., Nov. 4, 2004, 1 page.

Surgical Specialties Corporation, "Wound Closure Catalog"; Summer 2005, 5 pages.

Rodeheaver, G.T. et al., "Barbed Structures for Wound Closure: In Vivo Wound Security, Tisse Compatibility and Cosmesis Measurements," Society for Biomaterials 30$^{th}$ Annual Meeting Transactions, 2005, 2 pages.

Belkas, J. S. et al., "Peripheral nerve regeneration through a synthetic hydrogel nerve tube", Restorative Neurology and Neuroscience 23 (2005) 19-29.

Ingle, Nilesh P et al., "Testing the Tissue-holding Capacity of Barbed Sutures", College of Textiles, North Carolina State University, Fiber Science, The Next Generation Oct. 17-19, 2005, New Jersey Institute of Technology, Newark, NJ, 4 pages.

Liu, Changdeng et al., "Shape Memory Polymer with Improved Shape Recovery", Mater. Res. Soc. Symp. Proc. vol. 855E, 2005 Materials Research Society, pp. W4.7.1-W4.7.6.

De Persia, Raúl et al., "Mechanics of Biomaterials: Sutures After the Surgery", Applications of Engineering Mechanics in Medicine, GED-University of Puerto Rico, Mayaguez May 2005, p. F1-F27.

Scherman, Peter et al., "Sutures as longitudinal guides for the repair of nerve defects-Influence of suture numbers and reconstruction of nerve bifurcations", Restorative Neurology and Neuroscience 23 (2005) 79-85.

Sulamanidze, MD, M.A., et al., "Soft tissue lifting in the mid-face: old philosophy, new approach-internal stitching technique (APTOS NEEDLE)", Plastic and Aesthetic Surgery Clinic TOTAL SHARM, Moscow, Russia, (2005):15-29.

Bacci, Pier Antonio, "Chirurgia Estetica Mini Invasiva Con Fili Di Sostegno", Collana di Arti, Pensiero e Scienza; Minelli Editore—2006; 54 pgs.

Bellin, I. et al., "Polymeric triple-shape materials", Proceedings of the National Academy of Sciences of the United States of America Nov. 28, 2006; 2103(48):18043-18047.

Delorenzi, C.L., "Barbed Sutures: Rationale and Technique", Aesthetic Surg J. Mar. 2006 26(2): 223-229.

Gross, Alex, "Physician perspective on thread lifts", Dermatology Times Feb. 2006 27(2): 2 pages.

Khademhosseini, Ali et al., "Nanobiotechnology Drug Delivery and Tissue Engineering", Chemical Engineering Progress 102:38-42 (2006).

Murtha et al., "Evaluation of a Novel Technique for Wound Closure Using a Barbed Suture", Journal of the American Society of Plastic Surgeons 2006; 117(6); 1769-1780.

Ruff, Gregory, "Technique and Uses for Absorbable Barbed Sutures", Aesthetic Surgery Journal Sep./Oct. 2006; 26:620-628.

Behl, Marc et al., "Shape-Memory Polymers", Materials Today Apr. 2007; 10(4); 20-28.

Kaminer, M. et al., "ContourLift™: A New Method of Minimally Invasive Facial Rejuvenation", Cosmetic Dermatology Jan. 2007; 20(1): 29-35.

Kelch et al., "Shape-memory Polymer Networks from Olio[(0-hydroxycaproate)-co-glycolate]dimethacrylates and Butyl Acrylate with Adjustable Hydrolytic Degradation Rate", Biomacromolecules 2007;8(3):1018-1027.

Maitland et al., "Prototype laser-activated shape memory polymer foam device for embolic treatment of aneurysms", Journal of Biomedical Optics May/Jun. 2007;12(3): pp. 030504-1 to 030504-3.

Moran et al., "Bidirectional-Barbed Sutured Knotless Running Anastomosis v Classic van Velthovan in a Model System", Journal of Endourology Oct. 2007; 21(10); 1175-1177.

Mullner, "Metal Foam Has a Good Memory", Dec. 18, 2007 Original story at <http://www.physorg.com/news117214996.html>.

Paul, Malcolm D. and Rui Avelar, "Quill 198 SRS Techniques & Procedures a Novel Approach to Soft Tissue Approximation", Canada, Angiotech Pharmaceuticals, Inc., First Edition [8]2007: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Second Edition [8]2008: 20 pages.

Paul, Malcolm D. and Rui Avelar, "Quill™ SRS Techniques & Procedures a Novel Approach to Soft Tissue Approximation", Canada, Angiotech Pharmaceuticals, Inc., Third Edition 2009, [8] 2007-2009: 27 pages.

Paul, Malcolm D. and Rui Avelar, "Quill™ SRS Techniques & Procedures a Novel Approach to Soft Tissue Approximation", Canada, Angiotech Pharmaceuticals, Inc., Fourth Edition 2010, [8] 2007-2010: 27 pages.

Dahlin, Lars, "Techniques of Peripheral Nerve Repair", Scandinavian Journal of Surgery 97: 310-316, 2008.

Madduri, Srinivas, et al., "Neurotrophic factors release from nerve conduits for peripheral axonal regeneration", European Cells and Materials vol. 16; Suppl. 1 (2008), p. 14.

Nie, Zhihong and Kumacheva, Eugenia, "Patterning surfaces with functional polymers", Nature Materials vol. 7(2008): 277-290.

Paul, Malcolm D., "Using Barbed Sutures in Open/Subperiosteal Midface Lifting", Aesthetic Surgery Journal 2006(26): 725-732.

Richert, Ludovic, et al., "Surface Nanopatterning to Control Cell Growth", Advanced Materials 2008(15): 1-5.

Tan Ee Lim et al., "A wireless, passive strain sensor based on the harmonic response of magnetically soft materials", Smart Materials and Structures 17 (2008): pp. 1-6.

Villa, Mark T. et al., "Barbed Sutures: A Review of Literature", Plastic and Reconstructive Surgery; Mar. 2008; vol. 121, No. 3; pp. 102e-108e.

Demyttenaere, Sebastian V. et al., "Barbed Suture for Gastrointestinal Closure: A Randomized Control Trial", Surgical Innovation; vol. 16, No. 3; Sep. 2009; pp. 237-242.

Einarsson, Jon I. et al., "Barbed Suture, now in the toolbox of minimally invasive gyn surgery", OBG Management; vol. 21, No. 9; Sep. 2009; pp. 39-41.

Paul, Malcolm D., "Bidirectional Barbed Sutures for Wound Closure: Evoluation and Applications", Journal of the American College of Certified Wound Specialists (2009) 1, 51-57.

Sulamanidze, Marlen et al., "APTOS Suture Lifting Methods: 10 Years of Experience", Clin Plastic Surg 36 (2009); pp. 281-306.

Ingle, N.P. et al., "Optimizing the tissue anchoring performance of barbed sutures in skin and tendon tissues", Journal of Biomechanics 43 (2010); pp. 302-309.

International Search Report for PCT/US2002/027525 dated Dec. 9, 2002, 3 pages.

European Search Report for EP107006258.3 dated May 4, 2007, 4 pages.

U.S. Appl. No. 12/972,802, filed Dec. 20, 2010, Genova et al.

US 6,447,535, 09/2002, Jacobs (withdrawn)

US 6,503,260, 01/2003, Schaller (withdrawn)

* cited by examiner

SYSTEM FOR CUTTING A SUTURE TO CREATE TISSUE RETAINERS OF A DESIRED SHAPE AND SIZE

CLAIM TO PRIORITY

This application is a continuation of U.S. application Ser. No. 11/691,845, filed on Mar. 27, 2007, now; which is a continuation of U.S. application Ser. No. 10/486,123, filed Jul. 2, 2004, now U.S. Pat. No. 7,225,512, issued Jun. 5, 2007; which claims priority under 35 USC §371 to PCT/US2002/027525, filed on Aug. 29, 2002, published on Mar. 6, 2003 under Publication No. WO03/017850A1, now expired; and is a continuation-in-part of U.S. application Ser. No. 09/943,733, filed Aug. 31, 2001, now U.S. Pat. No. 6,848,152, issued Feb. 1, 2005. All of the above claimed priority applications are incorporated herein by reference in their entireties.

BACKGROUND OF THE INVENTION

1. Field of the Invention

The invention relates to a method of barbing suture filament by varying the blade geometry and/or the movement of a blade when cutting a suture filament where the method can also be utilized to cut a plurality of axially spaced barbs on the exterior of sutures and an apparatus for performing this.

2. Description of the Prior Art

In the prior art, it is well known that surgical and traumatic wounds are typically closed with a filament introduced into the tissue by a needle attached to one end. Closure of the wound and holding tissues together supports healing and re-growth. What is typically used for this procedure is known as a suture.

A barbed suture is a one-way suture which allows passage of a needle-drawn suture in one direction through tissue, but not in the opposite direction. A barbed suture is generally an elongated body having a pointed leading end and a plurality of axially and circumferentially spaced barbs on the exterior surface of the elongated body.

In closing a wound with a barbed suture, the suture is passed through tissue at each of the opposed sides of a wound. Suture pairs are formed in which trailing ends of sutures are positioned generally in alignment at opposite sides of the wound. On insertion of each suture, the needle is pushed to extend out of the tissue at a point laterally remote from the wound, then the needle is pulled out to draw the suture to the desired position, and the suture is then severed from the needle. (Note that methods of using barbed sutures are disclosed in copending U.S. patent application Ser. No. 09/896,455, filed Jun. 29, 2001, entitled "Suture Method" and assigned to Quill Medical, Inc., the disclosure of which is incorporated herein by reference.) The advantage of using barbed sutures is that there is an ability to put tension in the tissue with the result of less slippage of the suture in the wound. The number of suture pairs is selected in accordance with the size of the wound and the strength required to hold the wound closed. Although tissue anchoring is easier done with a very pointed barb and a relatively skinny tip, better tissue holding results are obtained with a fuller tip barb.

In some circumstances of tissue repair, a random configuration of barbs on the exterior of the suture might be preferred. With as many barb angles as possible, superior wound holding would be achieved. However, in other circumstances where the wound or tissue repair needed is small, a small suture would be preferable. A small suture would require a reduced number of barbs on the exterior of the suture. Various methods of cutting the barbs have been proposed (see e.g. U.S. Pat. No. 5,931,855). However, such methods have not been commercially exploited for reasons which are unclear.

It is seen from the foregoing that there is a need for a method of cutting barbs on the exterior of sutures with a minimum of difficulty and in a reliable and relatively economic fashion so as to allow for the wide spread commercialization of such sutures. Such a method should also be able to vary the size of the barbs, their location and depth to allow for variation thereof and versatility of their application. The method should be able to cut a plurality of barbs with the positioning depending on the number of barbs needed. The need also exists for a device able to use the method described above which can provide a plurality of axially spaced barbs either in a random or similar configuration, with the configuration depending upon, among other things, the type of tissue being repaired.

SUMMARY OF THE INVENTION

It is therefore a principal object of the present invention to provide for a practical method of cutting barbs in a suture.

It is therefore a further object of the present invention to provide a method for cutting fuller tipped barbs of various sizes on the exterior of a suture.

It is therefore a still further object of the present invention to provide a method for cutting a plurality of axially spaced barbs on the exterior of a suture.

It is therefore a still further object of the present invention to provide a method for cutting a plurality of axially spaced barbs circumferentially about the exterior of a suture.

It is therefore a still further object of the present invention to provide a method for cutting a plurality of axially spaced barbs in similar or random configurations on the exterior of a suture.

It is therefore a yet further object of the invention to provide for an illustrative apparatus to perform this method.

To attain the objects described, there is provided a cutting method which produces suture barbs of varying sizes depending on the geometry of the blade being used and/or the movement of the blade when cutting into a suture. By altering the blade geometry and/or degree or trajectory of blade movement, the barbs can be made of varying sizes designed for various surgical applications. For example: for joining fat and relatively soft tissues, larger barbs are desired, whereas smaller barbs are more suited for collagen intensive tissues. Also, the use of a combination of large and small barbs on the same suture will ensure maximum anchoring properties wherein barb sizes are customized for each tissue layer.

The cutting method may be achieved with a cutting device disclosed herein. The device disclosed can produce six sets of barbs in staggered positions along the length of a suture, such that three sets of barbs are faced opposite to another three sets of barbs. Viewing the suture on a cross-sectional plane, the barb sets would be positioned either 120 or 180 degrees to each other, depending on the cutting method. Longitudinally, each barb cut would begin where the nearest one ends.

Compared with the method of cutting barbs in an untwisted state, using the twisted configuration can simplify production equipment; produce a stronger suture; reduce production cycle time by at least a factor of three; and be easily scalable to smaller diameters and produce barbs in a spiral fashion rather than at 120 or 180 degrees.

By way of variations, slight modifications, and/or combinations of the methods of cutting with and without twisting the suture, barbs can be obtained with random configurations. There are instances in tissue repair that the random configuration may be ideal to anchor tissues in as many barb angles as possible to provide superior wound holding properties. These and other objects and characteristics of the present invention will become apparent from the further disclosure to be made in the detailed description given below.

BRIEF DESCRIPTION OF THE DRAWINGS

Thus by the present invention its objects and advantages will be realized the description of which should be taken in conjunction with the drawings wherein.

DETAILED DESCRIPTION OF CERTAIN PREFERRED EMBODIMENTS

We refer now to the drawings in detail wherein like numerals refer to like elements throughout the several views.

The purpose of the present invention is to provide for an effective way of producing a barbed suture. In this regard, several different types of methods are disclosed which are directed to the cutting action of a blade on the suture to create the barbs. As will be described, the cutting action envisioned takes into account the movement of the blade and the blade geometry.

Essentially, the cutting of the suture with a blade takes into account three dimensions x-y-z of the suture 6. Each dimension is important and may be addressed by the cutting motion of the blade and/or the blade geometry. Depending on the blade geometry, the blade movement can have an effect in the other dimensions.

Figure 1A:
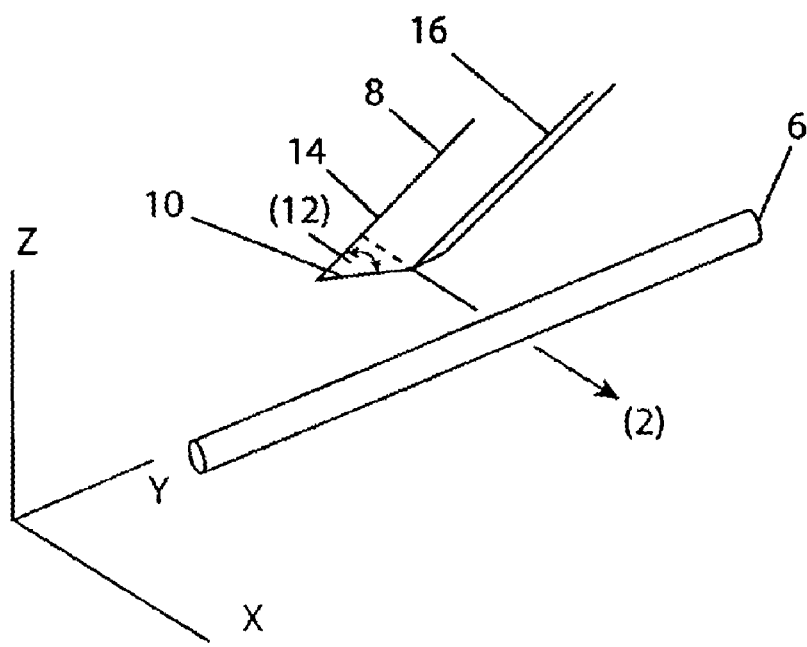
FIGS. 1A-F depict the cutting motion of a blade with one degree of freedom from movement and two degrees of freedom from blade geometry.

In this regard, FIG. 1A illustrates a consistent cutting motion of a blade 8 with one degree of freedom of movement and two degrees of freedom from blade geometry across a suture 6. One degree of freedom from movement is movement in one direction in a three-dimensional "x-y-z" layout. For FIG. 1A, direction 2 follows the lateral "x" axis in the cut of suture 6, with the movement of blade 8 in direction 2 before accomplishing a cut. An edge 10 of blade 8 has an angle, depicted as 12, in its blade geometry between the tips of sides 14, 16 of blade 8, as well as an angle (not shown) in its blade geometry between the top and bottom planes of blade 8. Such a geometry will cause an effect in the y and z dimensions (i.e. in the length and depth of the barb) just by the movement of blade 8 in the x direction.

Figure 1B:
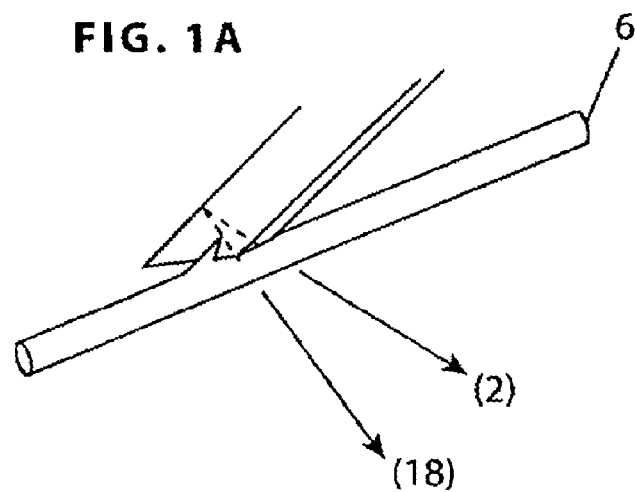
Figure 1C:
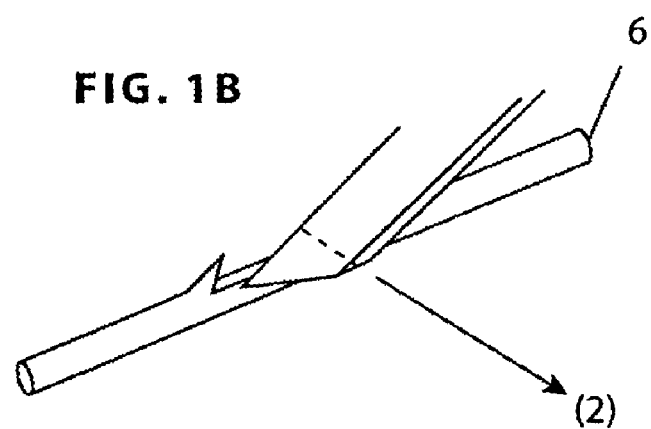

As shown in FIG. 1B, these angles allow a cut into suture 6 in the y and z directions during movement in direction 2. This cutting-into movement is depicted as resultant direction 18. FIG. 1C depicts the completed cut of suture 6 with a continued movement in direction 2 away from the suture 6.

Figure 1D:
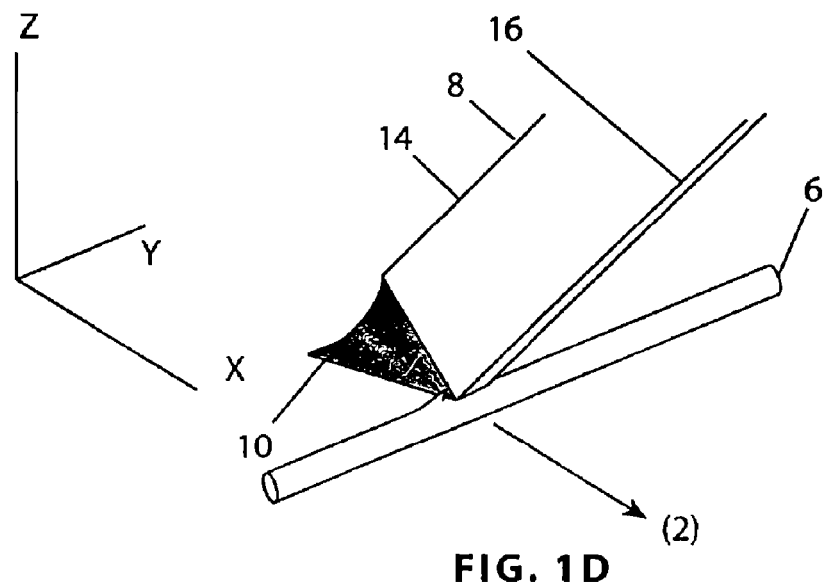

Similar to FIG. 1A, FIG. 1D illustrates a cutting motion of a blade 8 with one degree of freedom of movement and two degrees of freedom from blade geometry across a suture 6. In FIG. 1D, blade 8 is a hollow ground blade, in which edge 10 has an angle in its blade geometry between the tips of its sides 14, 16, as well as a concave or curved-in face in its blade geometry between the top and bottom planes of blade 8. Such a geometry will cause an effect in the y and z dimensions (i.e. in the length and depth of the barb) just by the movement of blade 8 in the x direction.

Figure 1E:
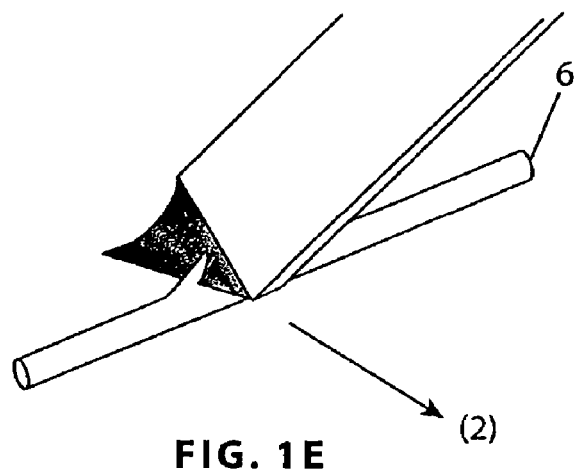
Figure 1F:
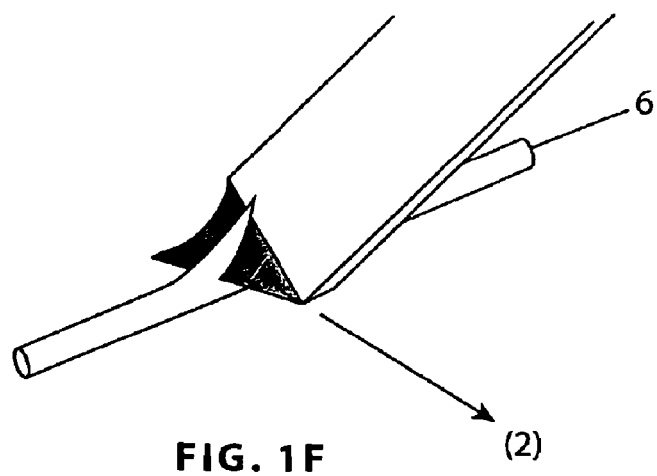

As shown in FIGS. 1E and 1F, this blade geometry allow a cut into suture 6 in the y and z directions during movement of blade 8 in direction 2. Comparison of FIG. 1E with FIG. 1F illustrates how movement of blade 8 in direction 2 increases the length and depth of the barb.

Figure 2A:
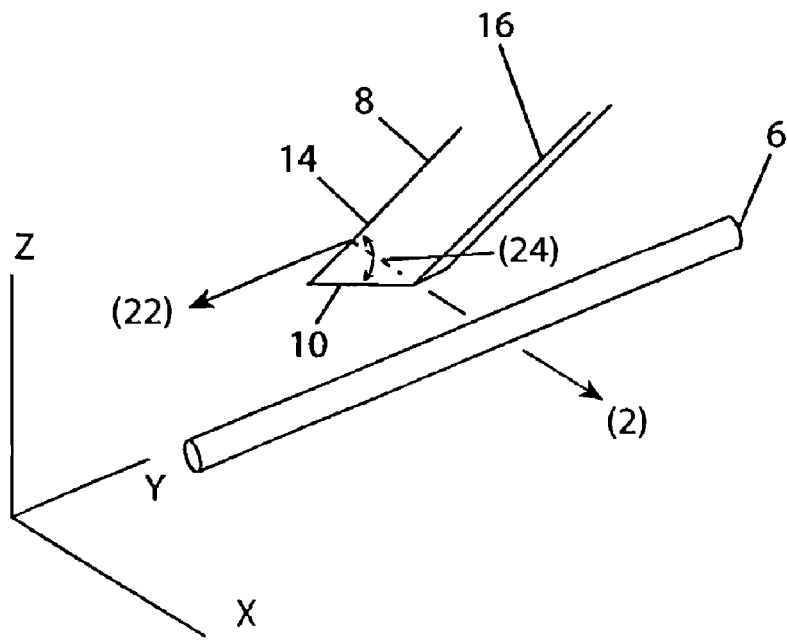
FIGS. 2A-C depict the cutting motion of a blade with two degrees of freedom from blade movement and one degree of freedom from blade geometry.
Figure 2B:
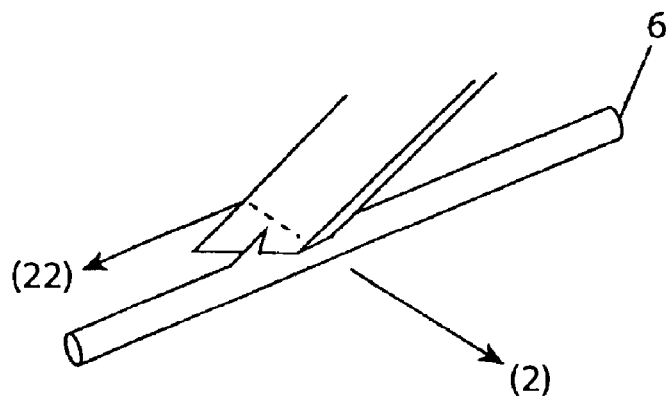
Figure 2C:
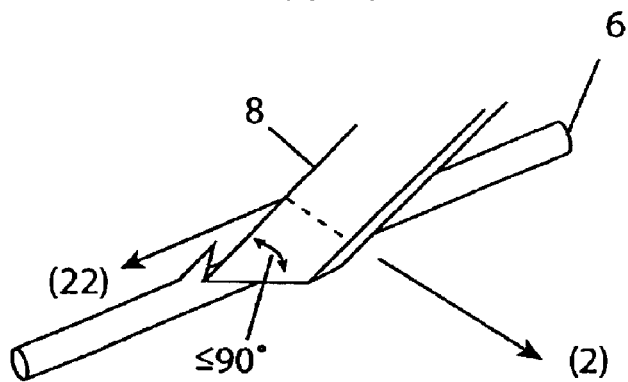

Turning now to FIGS. 2A-C, a consistent cutting motion of a blade with two degrees of freedom of movement and one degree of freedom from blade geometry is illustrated. Two degrees of freedom of movement is movement in two directions x and y. For FIG. 2A, direction 2 follows the lateral "x" axis and direction 22 follows the forward "y" axis in the cut of suture 6. In this regard the movement of blade 8 in two directions 2 and 22 simultaneously may be used to accomplish a cut. Edge 10 of blade 8 is at an angle of 90° or less, depicted as 24, of one degree in its blade geometry between the tips of sides 14, 16 of blade 8.

As shown in FIG. 2B, forward movement in direction 22 and along a lateral direction 2 allows a longer cut into suture 6 than produced in FIG. 1, since in FIG. 1 the blade geometry and blade movement in the x-axis determines the length of the barb, whereas in FIG. 2 the blade geometry and blade movement along both the "y" and "x" axes determines the length of the barb. This longer cutting action is in the "y" direction. FIG. 2C shows the completed cut of the suture 6 with a continued movement in direction 2 away from the suture.

Figure 3A:
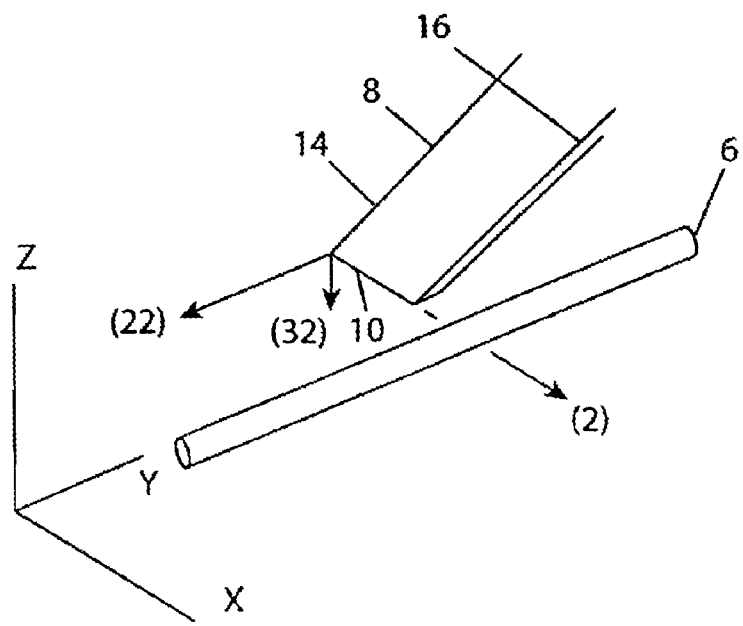
FIGS. 3A-C depict they cutting motion of a blade with three degrees of freedom from blade movement and a solid plane geometry.
Figure 3B:
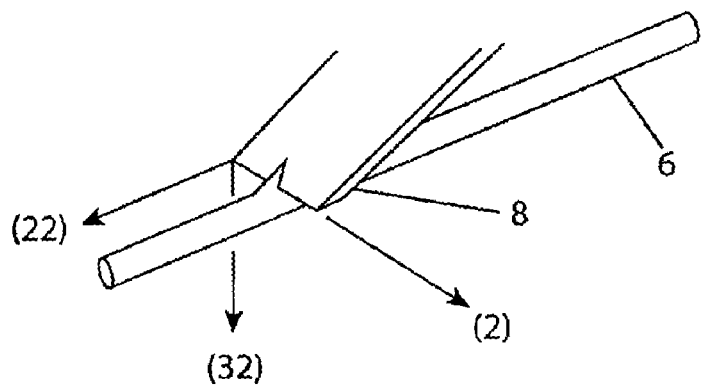

FIG. 3A illustrates a further consistent cutting motion of a blade with three degrees of freedom of blade movement and edge 10 of 90° or less. Three degrees of freedom from movement is movement in the three directions of a three-dimensional "x-y-z" layout. For FIG. 3A, direction 2 follows the lateral "x" axis, direction 22 follows the forward "y" axis and direction 32 follows the downward "z" axis. The movement of blade 8 in all three directions 2, 22 and 32 may be used to accomplish the cutting of a barb on the suture 6.

Figure 3C:
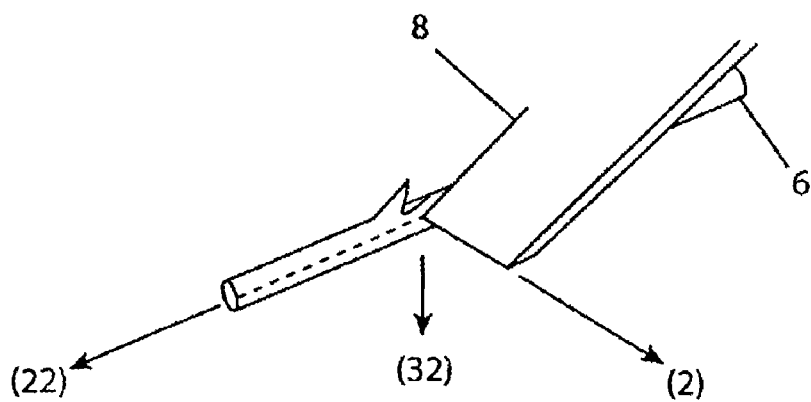

The combination of movement in lateral direction 2, forward direction 22 and downward direction 32 would allow one to vary the length and depth of the cut to create a barb. It may be a deeper barb by cutting further in direction 32 and/or a longer barb by cutting further in direction 22. By moving blade 8 in lateral direction 2, forward direction 22 and downward direction 32 simultaneously forms a trajectory, which may be altered to create barbs with different qualities such as aspect ratios. FIG. 3C shows the completed cut of suture 6 with a continued movement in directions 2, 22, and 32 away from the suture 6.

Figure 4A:
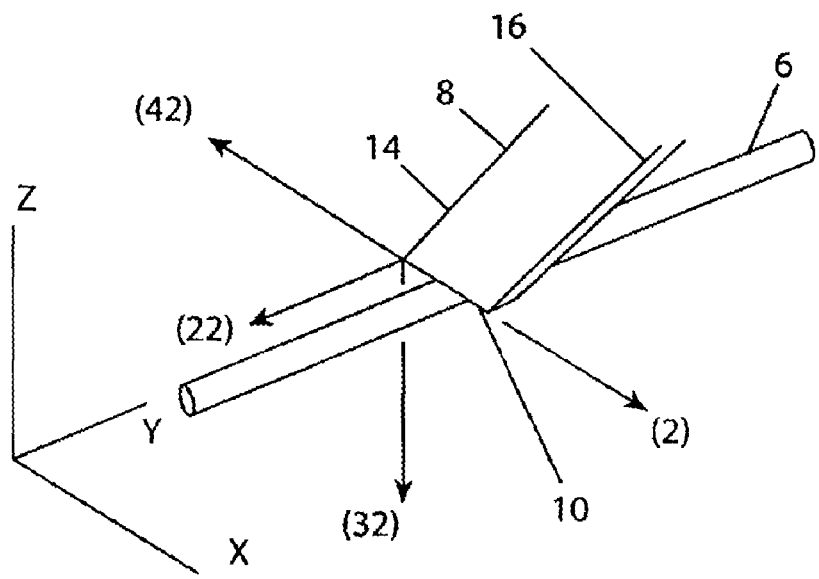
FIGS. 4A-C depict a zigzag (oscillating back and forth and downward) cutting motion of a blade with three degrees of freedom from blade movement and solid plane blade geometry.
Figure 4B:
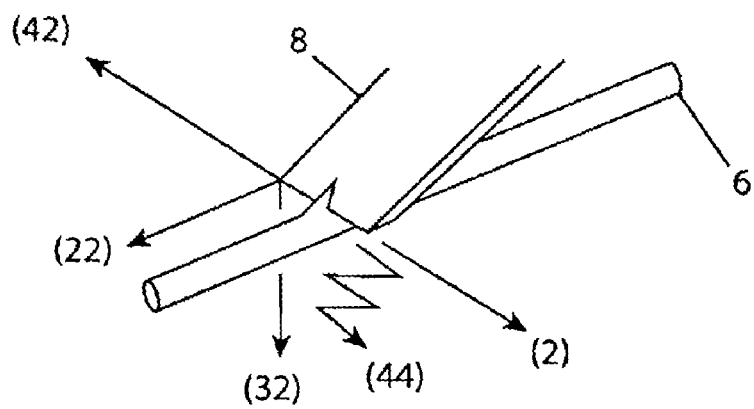
Figure 4C:
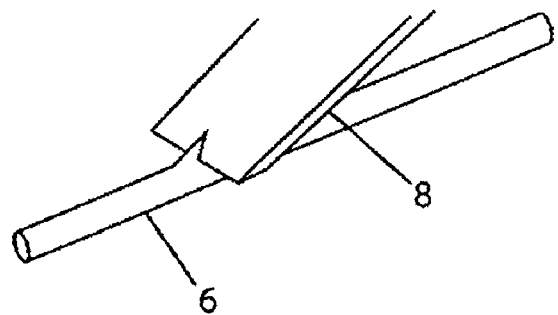

A yet further method of cutting a barb is shown in FIGS. 4A-C where a back and forth or zigzag (oscillating on the "x" axis combined with the movement in z and/or y axis) motion of the blade with three degrees of freedom of blade movement and a solid plane geometry cuts the barb with a saw-like cutting motion. Three degrees of freedom of movement is movement in three directions in the three-dimensional "x-y-z" layout. In FIG. 4A, direction 2 follows the lateral "x" axis, direction 22 follows the forward "y" axis, direction 32 follows the downward "z" axis, and direction 42 follows the lateral "x" axis except in a direction opposite to direction 2. FIG. 4A shows the movement which may be used to accomplish a cut of blade 8 in directions 22 and 32 with alternation in movement between directions 2 and 42. Edge 10 of blade 8 would be straight between the tips of sides 14, 16 of blade 8.

The combination of alternating movement in lateral directions 2 and 42, steady movement in forward direction 22 and steady movement in downward direction 32 allows the depth of the cut to be varied. The resultant zigzag cutting motion is shown as alternating direction 44 in FIG. 4B. FIG. 4C shows the completed cut of suture 6.

Figure 5A:
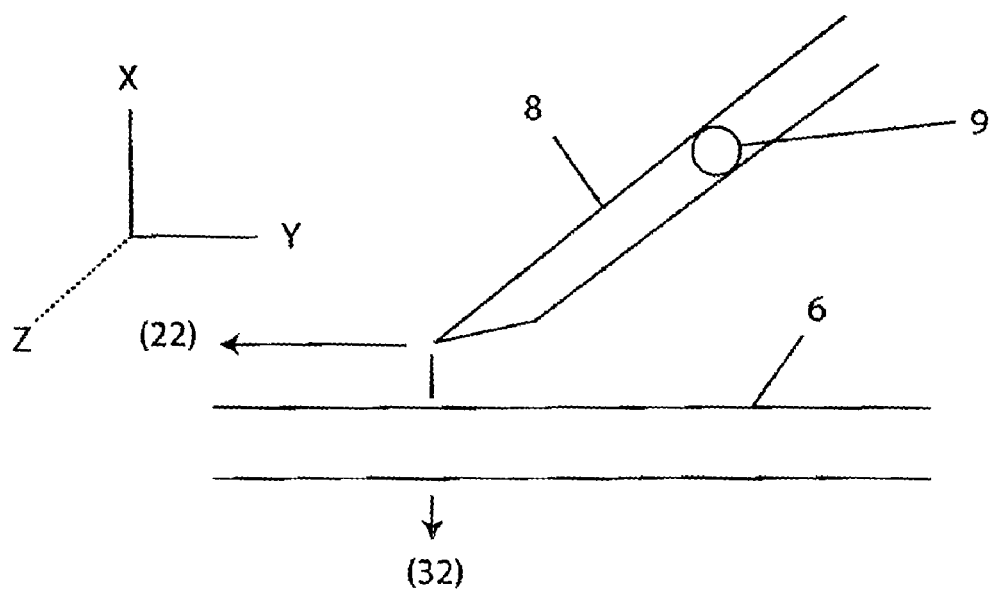
FIGS. 5A-C depict the cutting motion of an articulating blade with three degrees of freedom from blade movement.
Figure 5B:
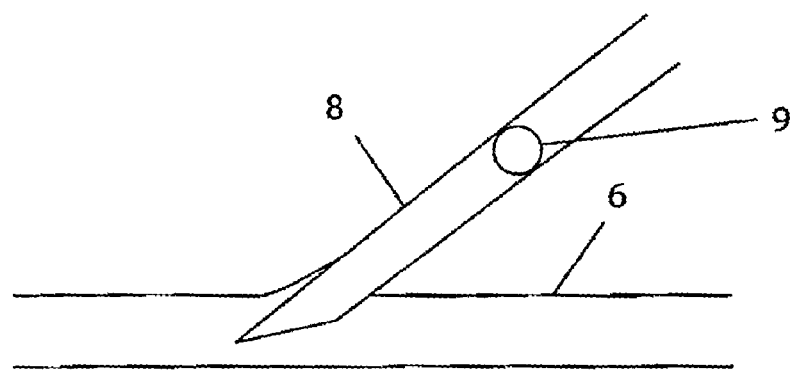
Figure 5C:
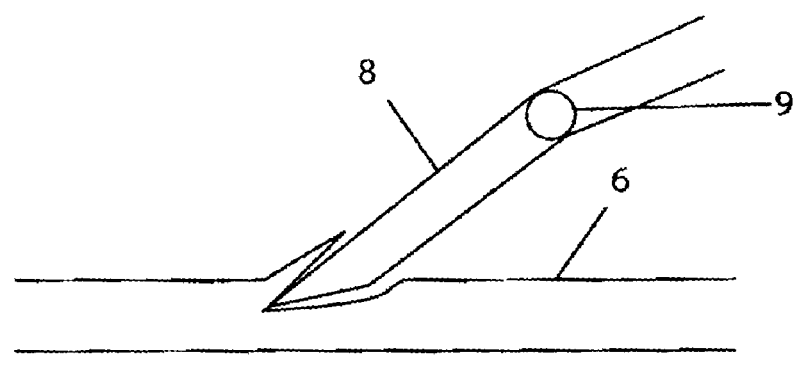
Figure 14:
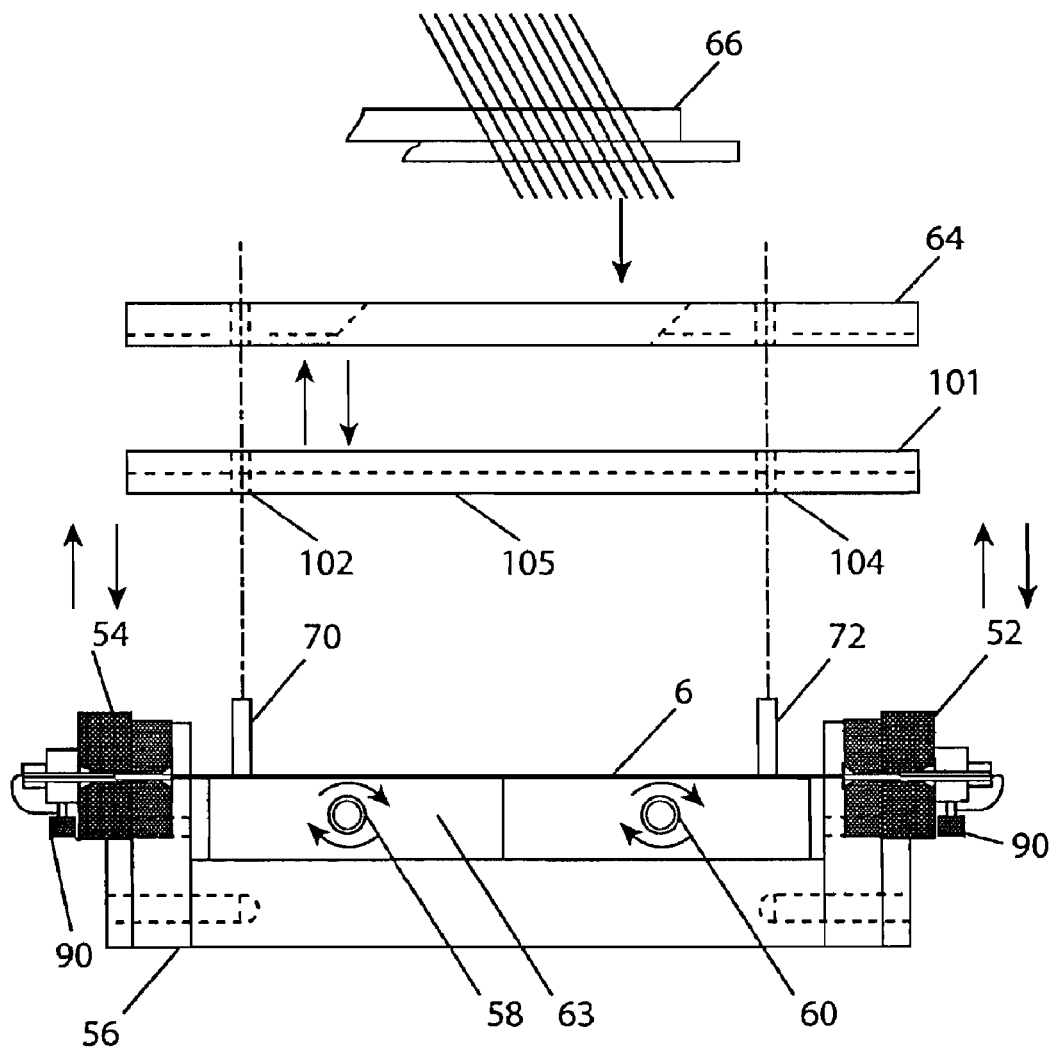
FIG. 14 depicts the placement of the various fixtures used with the cutting bed vise.

A still further method of cutting a barb is shown in FIGS. 5A-5C where articulation of blade 8 about an axis 9, in combination with any of the cutting motions described in FIG. 14 above, may be used to vary the depth of the barb. In FIG. 5A, direction 2 follows the lateral "x" axis (into the plane of the drawing), direction 22 follows the forward "y" axis and direction 32 follows the downward "z" axis. FIG. 5B shows the blade movement which may be used to accomplishing a cut of blade 8 in directions 2 and 22, similar to that depicted in FIG. 2B. Forward movement in direction 22 and along a lateral direction 2 produces a barb based on two degrees of freedom of blade movement. In FIG. 5C, blade 8 is also allowed to articulate about axis 9, providing an additional degree of freedom, which may be used to impart additional barb depth in direction 32 in the z-axis. This articulating motion of blade 8 may be employed in combination with any of the blade geometries and/or blade movements previously described. Articulation of blade 9 may also be used to lift a cut barb up and away from the surface of suture 6, thereby leading to a fuller or more pronounced barb.

The blade motion shown in FIGS. 1-5 can cut a suture filament made of polyglycolide, polydioxinone, polypropylene, other resorbables, other nonresorbables, Gore-Tex®, bi-component material or sutures made of other material suitable for the purpose.

While in the aforesaid examples, only a single blade is shown, it is envisioned that a plurality of blades may be utilized. They may be in tandem or on a rotary mechanism or on any other type of mechanical device which effects the implementation of the movement so described. Also, while the suture is shown in an untwisted state, it may be cut in a twisted state as hereinafter described.

By way of examples of mechanical devices for implementing the foregoing, reference is made to FIGS. 6-19 and 21-22. It should be understood, however, that these devices should not be considered exclusive and other types of devices for such implementation are contemplated.

Figure 6:
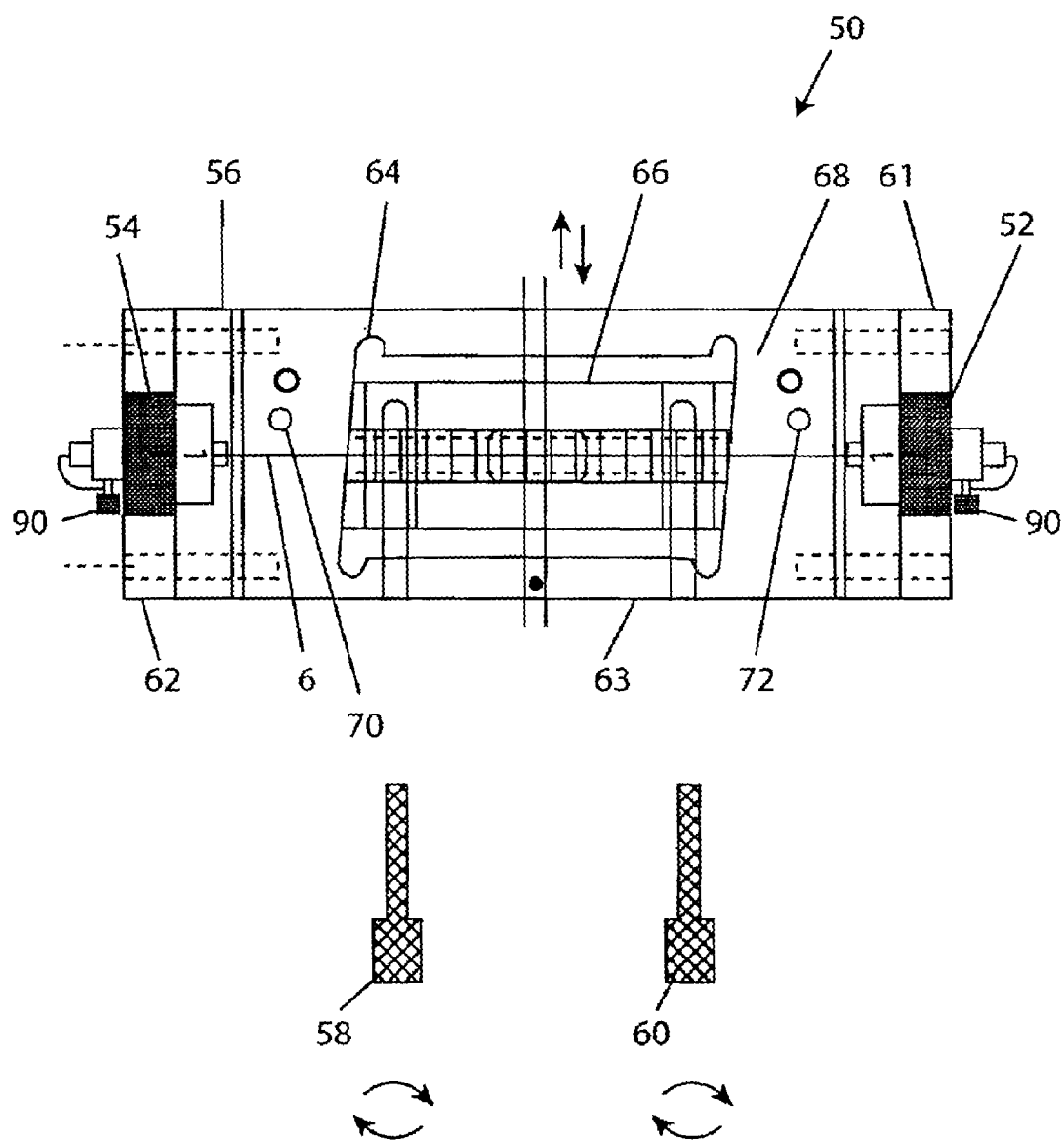
FIG. 6 is a top view of the assembled cutting device.
Figure 7:
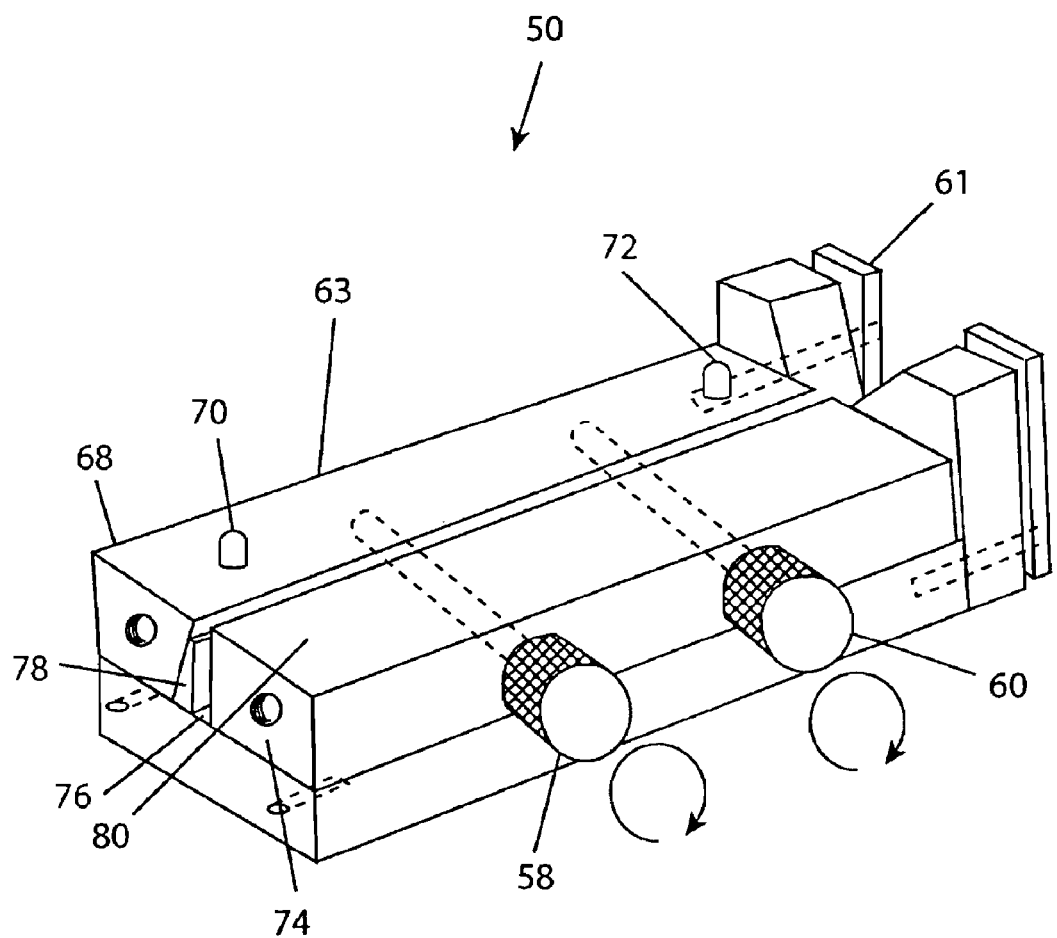
FIG. 7 is a perspective view of the cutting bed.

Turning now more particularly to FIG. 6, there is shown a cutting device 50 that allows an operator to cut multiple barbs on the exterior of suture 6 using the methods previously described. The cutting device 50 includes retention knobs 52, 54 for retaining the suture 6 on a vise 63 during cutting. Retention knobs 52, 54 include knob holders 61, 62. Cutting bed vise screws 58, 60 are used to open and to close cutting bed vise 63, where suture 6 is placed during cutting.

A cutting template 64 directs the cutting motion of a blade assembly 66 containing a plurality of blades across suture 6. Two additional cutting templates are provided for operation of the cutting device but are offset to provide a different axial position of the blades with respect to suture 6. The cutting templates have the same configuration as cutting template 64 and are installed in a similar manner throughout the several views. Also, while the templates shown are particularly suited for practicing one way of cutting the barbs, such templates can be readily modified to allow the performance of other ways, including those previously described as will be appreciated by a skilled artisan.

Cutting bed vise 63 assists in the alignment of the cutting templates. On the top of block 68 of cutting bed vise 63 are two protrusions. These protrusions are alignment pins 70, 72 which are used for setting the cutting templates and a tamp 101.

As will be apparent to one skilled in the art, the configuration of cutting bed vise 63 may vary. If the suture is rotated (e.g. 120 degrees or 180 degrees) to effect cutting barbs about its circumference, the cutting bed vise may be configured as shown in FIG. 6. If the suture is twisted prior to cutting, as will be discussed, the cutting bed vise 63 preferably has a configuration with trapezoidal sides such as those shown in FIG. 7. Because suture material is somewhat compliant, this design provides superior clamping to a vise with parallel sides. Note that the vise shown in FIG. 7 can also be used with a rotated suture, since there is a space to accommodate a cut barb. In this regard, in FIG. 7, blocks 68, 74 taper outward from the tops on their interior sides to a surface 76, with the blocks depicting a trapezoidal shape when viewed from an end profile. Protruding from the taper of block 68 is a trapezoidal or anvil suture clamp 78 which is used to secure suture 6 during the closing of cutting bed vise 63. Suture clamp 78 is a wedge shape which sets on surface 76 and ends slightly below top 80.

Figure 8:
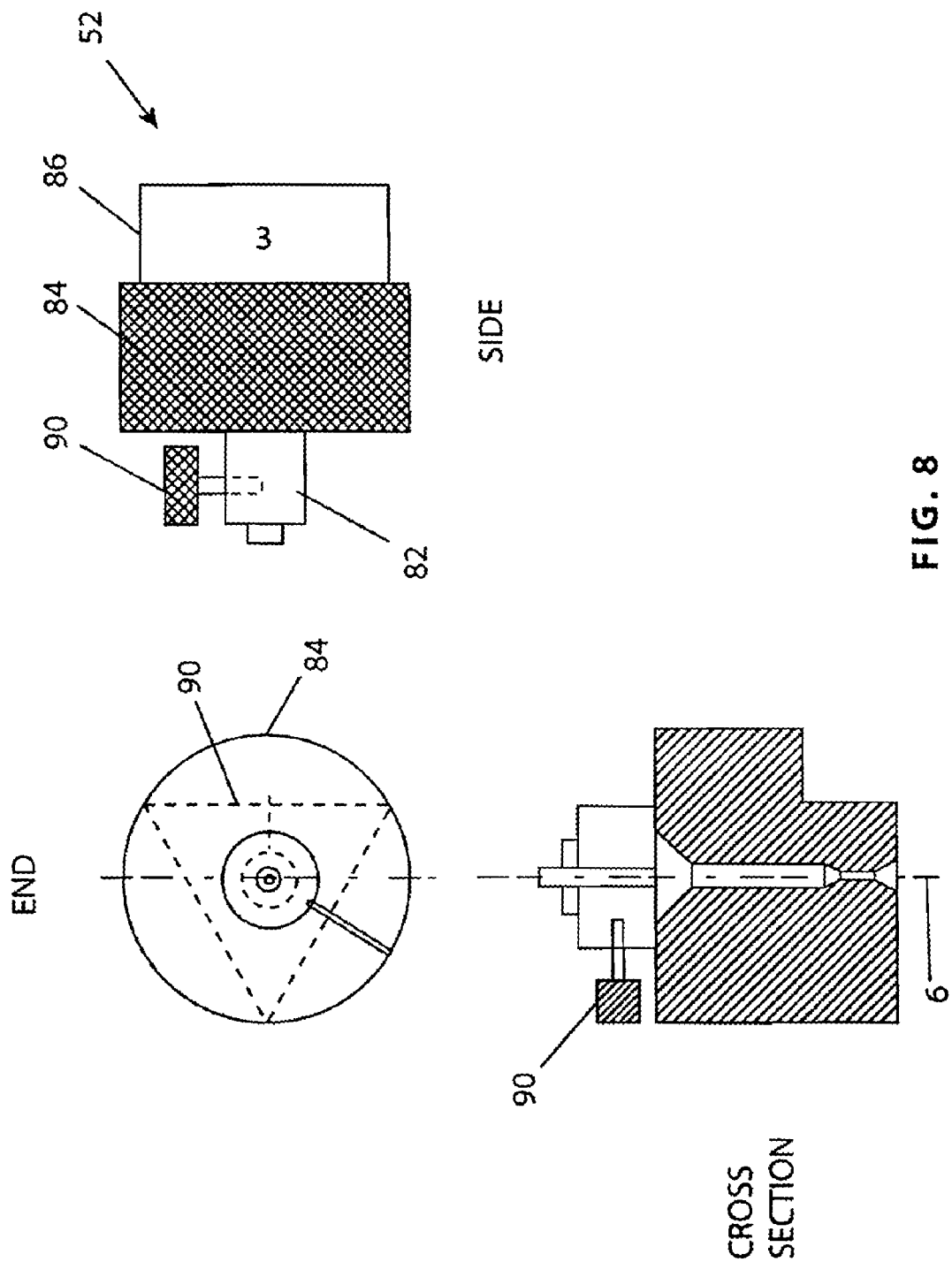
FIG. 8 depicts an end, a side, and a cross-sectional view of the retention knob of the cutting device.

In addition to securing suture 6, retention knobs 52, 54 are rotated between the various cutting methods and are numerically indexed for precise movement. As depicted in FIG. 8, retention knob 52 is a solid elongated body. Retention knob 52 comprises a cylinder 82 having a gripping area 84 integral with a triangular protrusion 86. Triangular protrusion 86 can rest on cutting bed 56 or a spacing bar 100, shown in FIG. 13. An anchor screw 90 secures suture 6 to the retention knob. The triangular protrusion includes numerical marks for guiding the operator in positioning the retention knob during various stages of the cutting method; however, the triangular protrusion may be indexed in other variations. One side of the triangular protrusion has the number "1" imprinted, another side has the number "2" imprinted and a third side has the number "3" imprinted. Retention knob 54 has the same characteristics as retention knob 52.

Figure 9:
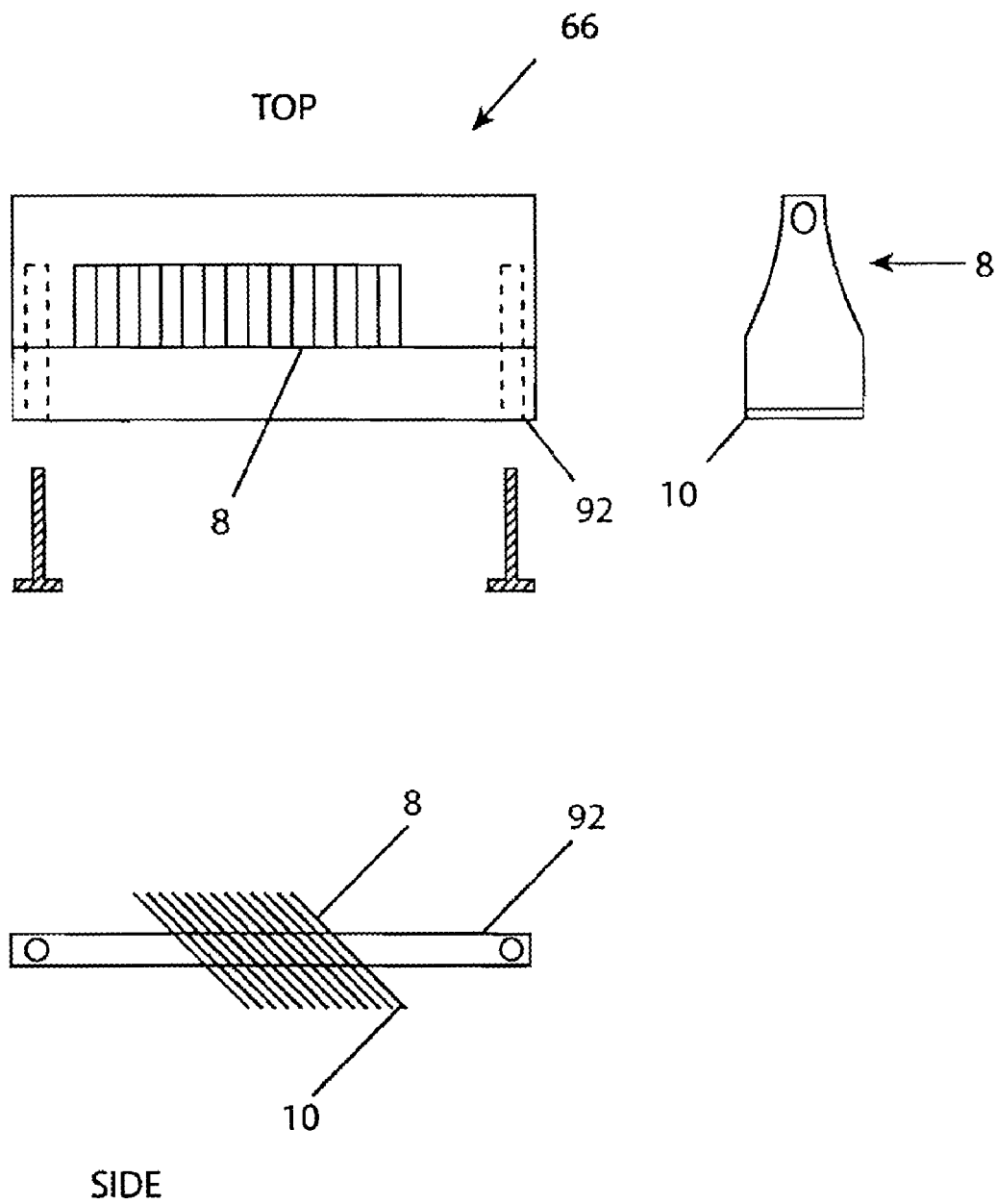
FIG. 9 depicts a top and side view of the blade assembly of the cutting device and a top view of an example blade for the blade assembly.
Figure 10:
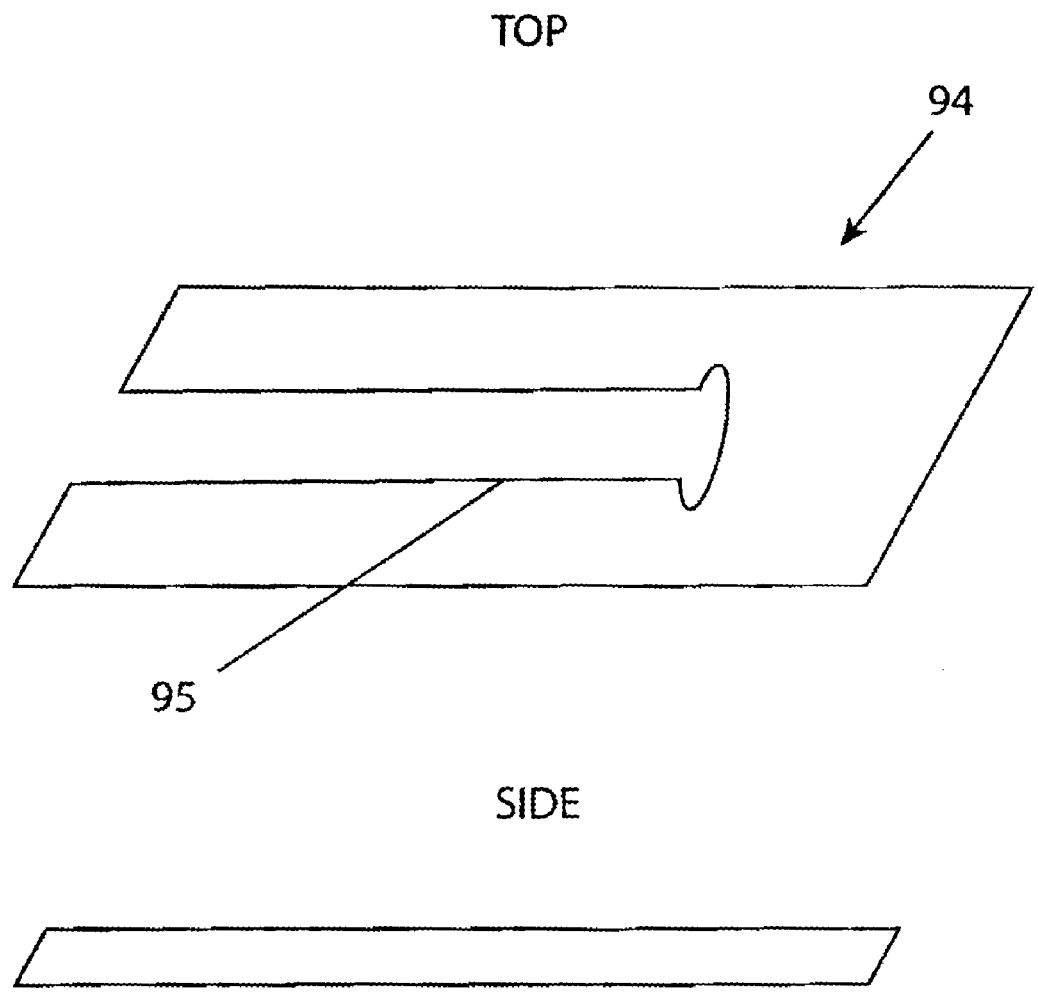
FIG. 10 depicts a top and side view of the template block of the blade assembly.

For cutting a plurality of barbed sutures at one time, a multi-blade assembly is used. As depicted in FIG. 9, blade assembly 66 consists of a plurality of blades 8 secured in retaining block 92. In FIG. 8, thirteen blades are depicted, although obviously the number of blades used may vary. Edge 10 of each of the blades used in the blade assembly 66 would extend through a template block 94, shown in FIG. 10 by the amount of the desired barb depth.

Retaining block 92 of FIG. 9 consists of two rectangular blocks which retain blade assembly 66 by a vise action. Blade assembly 66 conformingly fits to a cutaway section of the retaining block and blades 8 are inserted at a desired angle, which in this case is 148 degrees. The blades are secured in the retaining block 92 with the template block 94 attached thereto. Template block 94 acts as a guide for the blade assembly within the confines of the cutting templates.

Figure 11:
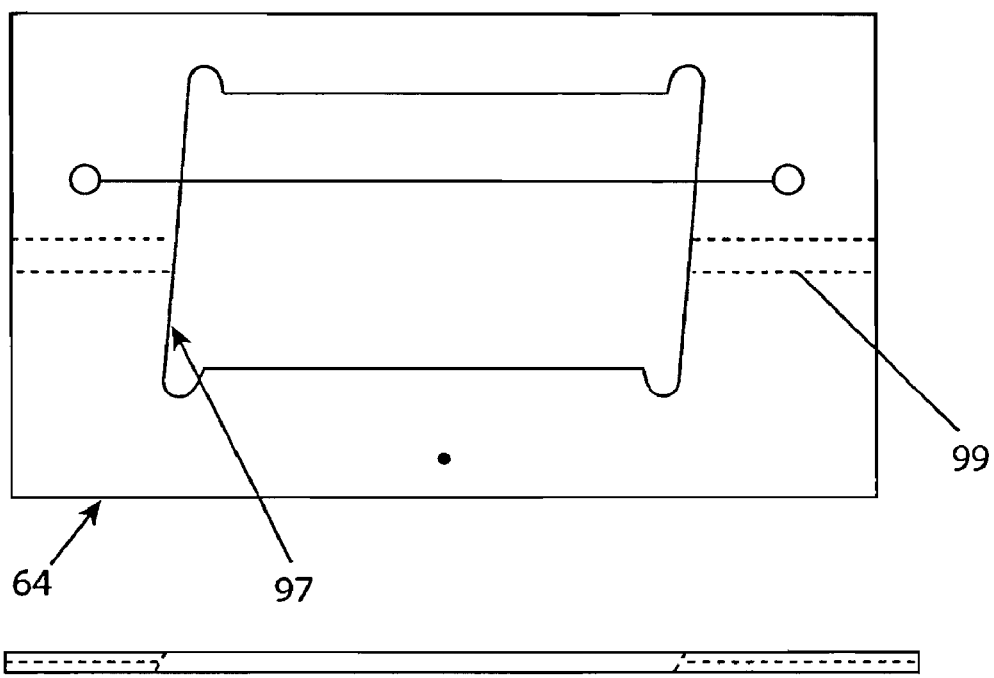
FIG. 11 depicts a top and side view of the cutting template used with the cutting device.

As shown in FIG. 11, the cutting template 64 provides a cutting path 97 for blade assembly 66. Cutting path 97 is shown as a parallelogram perimeter. Note, however, for example, the cutting path 97 may be shaped with a rectangular perimeter to suit the movements described in the cutting method of FIG. 1, or other shapes to permit additional degrees of blade movement as described in FIGS. 2-5. Additional cutting templates are provided and are similarly made with the purpose of offsetting the blade cut in an axial direction. The cutting template 64 is identified so as to indicate to the user which one is to be used at which stage of cutting. On opposite sides of the cutting template 64 is a channel 99 sized to accommodate the other sections of suture 6 not being cut by blade assembly 66.

Figure 12A:
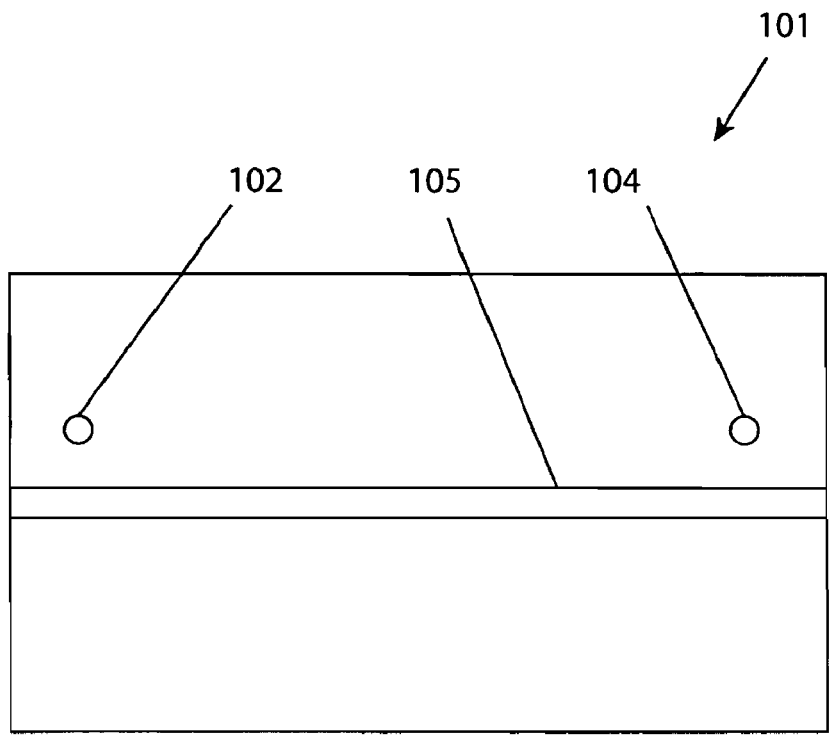
FIGS. 12A-B depict a top and side view of the tamp used with the cutting device.
Figure 12B:
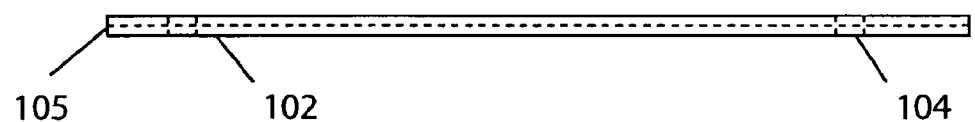

As shown in FIG. 12A, a tamp 101 is provided to insure that suture 6 is uniformly seated on the anvil 78. Apertures 102, 104 on tamp 101 are provided to engage the alignment pins 70, 72. A channel 105 is provided to hold suture 6 in place during the calibration. The depth of the channel 105 equals the thickness of the suture 6 above vise top 80.

Figure 13:
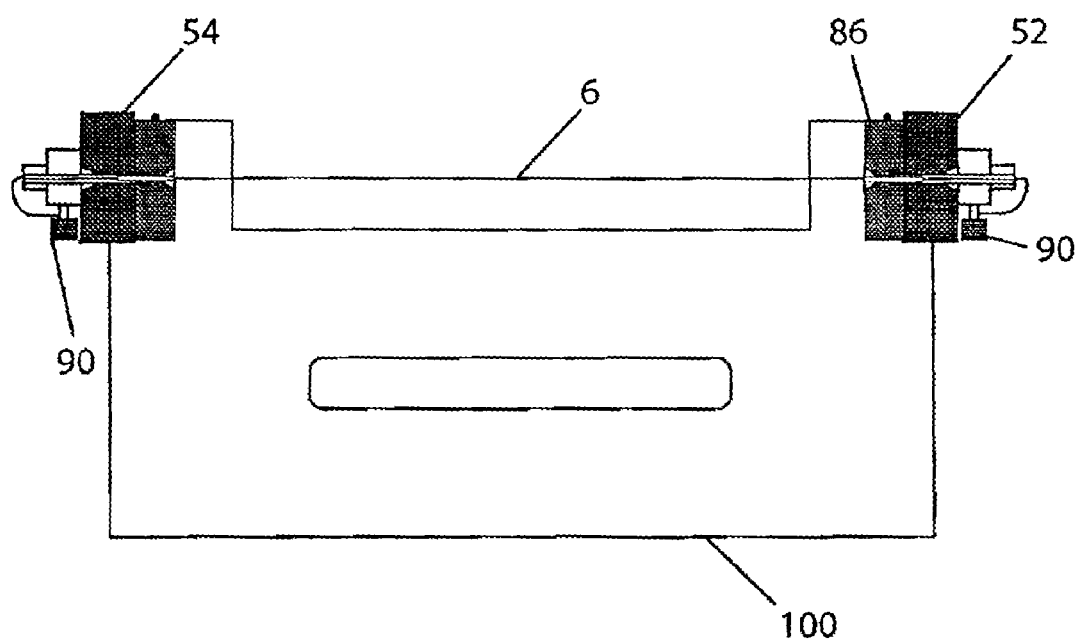
FIG. 13 depicts the securing of the suture to the retention knob and placement on the spacing bar.

To operate cutting device 50, first one secures the suture 6 to anchor screws 90 on one of retention knobs 52, 54 as shown in FIG. 13. Retention knob 52 is placed on the ledge of spacing bar 100 with the suture 6 drawn there-across with the second retention knob 54 positioned on the opposing ledge. The suture should not be overly taut once it is secured to the second retention knob by anchor screw 90. After sizing, suture 6 is placed on cutting bed 56 and held in place by cutting bed vise 63. The retention knobs 52 and 54 are indexed in a first position. As will be apparent in a second and third cutting for a barbed suture having barbs spaced 120 degrees apart, retention knobs 52 and 54 are rotated to second and third positions respectively.

As shown in FIG. 14, the tamp 101 is placed on the cutting bed 56 positioning the suture 6 in vice 63 which is tightened, and the tamp is then removed. Cutting template 64 is then placed onto cutting bed 56.

Figure 15:
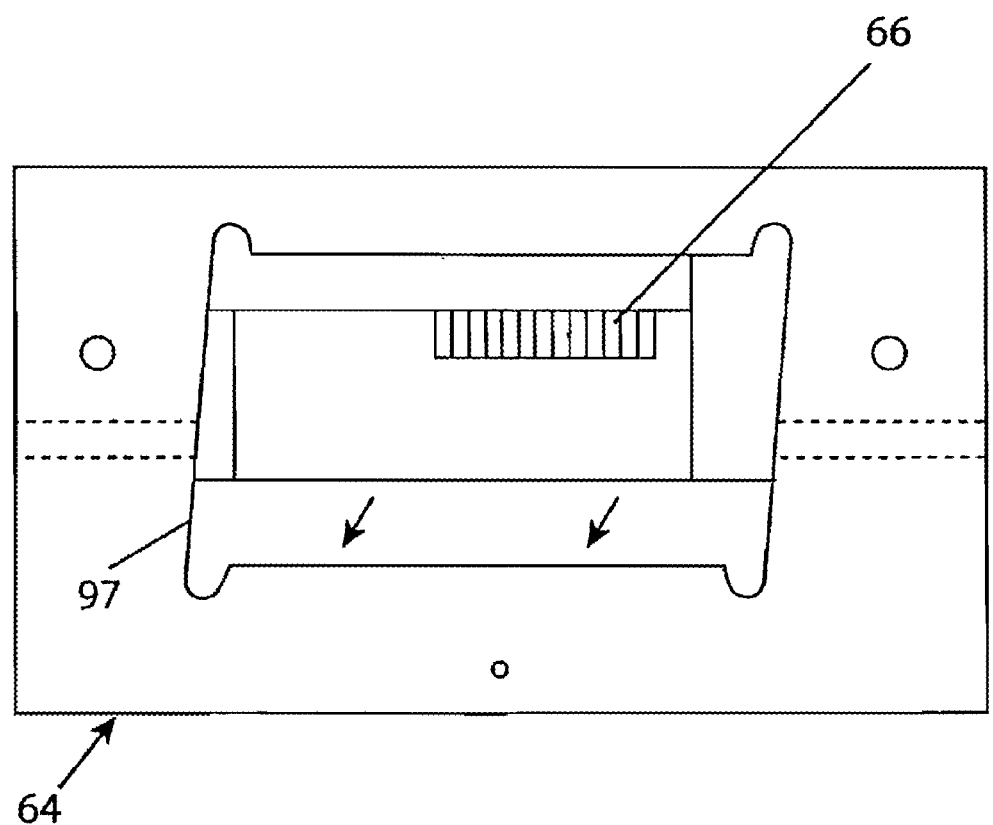
FIG. 15 depicts the blade assembly placement and downward movement in relation to the cutting template with the rest of the cutting device removed from the figure for clarity purposes.
Figure 16:
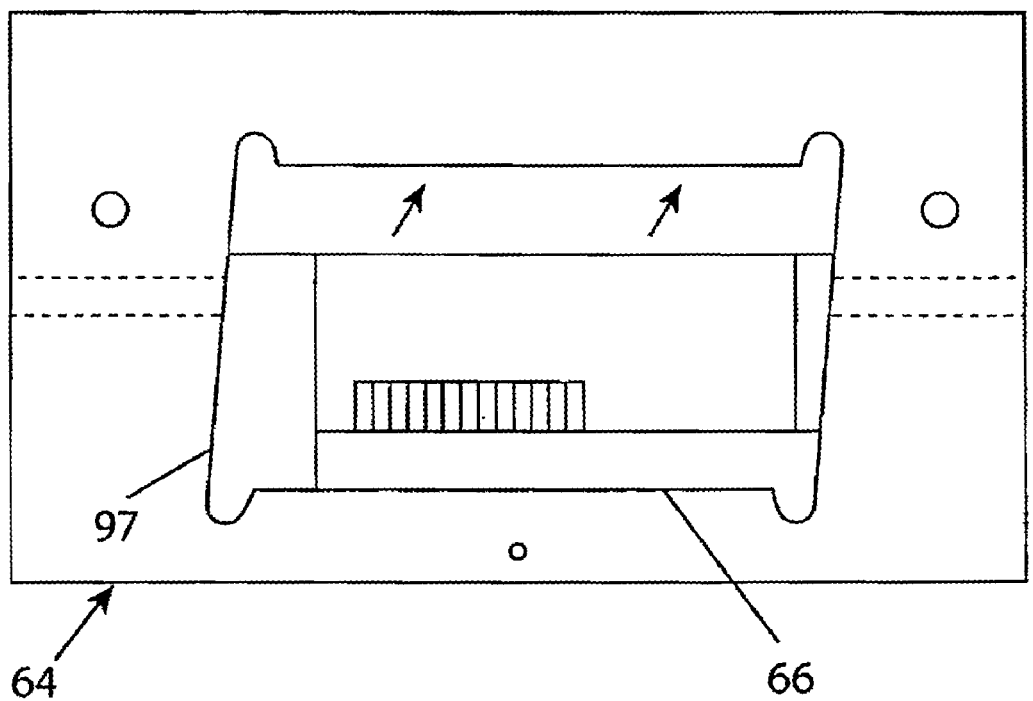
FIG. 16 depicts the blade assembly placement and upward movement in relation to the cutting template.

In the cutting method of suture 6, blade assembly 66 is placed onto cutting bed 56. The blade assembly is pressed down while slid from the top of the cutting template to the bottom along path 97 as shown in FIG. 15. The blade depth is set to produce the desired depth of the barb. After blade assembly 66 stops at the bottom of cutting template 64, the blade assembly is removed. To create barbs in a direction opposite those first cut, blade assembly 66 may then be turned 180 degrees and placed onto cutting bed 56 as shown in FIG. 16. The left and top of the blade assembly are in contact with the right and bottom of the cutting template along path 97. The blade assembly is pressed down while the blade assembly is slid from the bottom to the top. After the blade assembly 66 stops at the top of cutting template 64, the blade assembly and the template are removed.

As the process proceeds, suture 6 may be rotated, e.g. 120 degrees, 180 degrees, etc., and the cutting process repeated as shown in FIGS. 15-16. The suture should be set securely in the opening of cutting bed vise 63 and previously cut barbs should not project above top surface 80, and the process is repeated. For three sets of barbs about the circumference, the suture is rotated three times, for two sets, two times, etc.

Figure 17A:
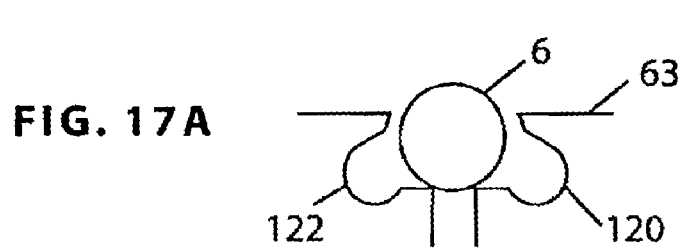
FIGS. 17A-F are front views depicting the setting of barbs in the cutting bed vise before and after cutting using the 120 degree rotation method of cutting.
Figure 17B:
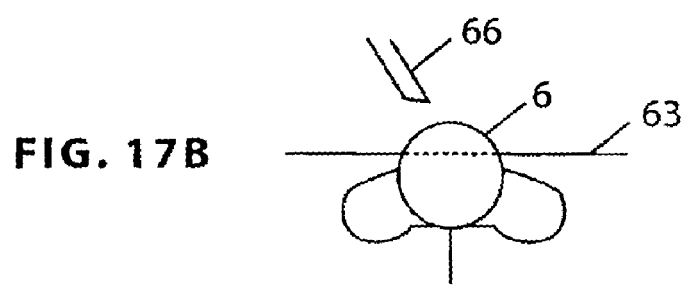
Figure 17C:
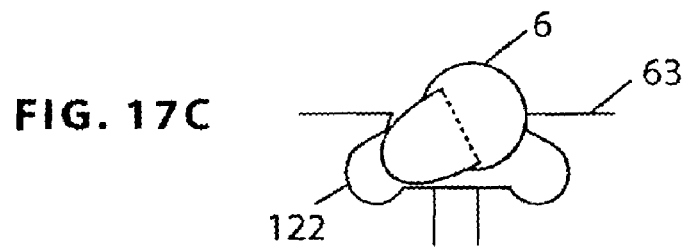
Figure 17D:
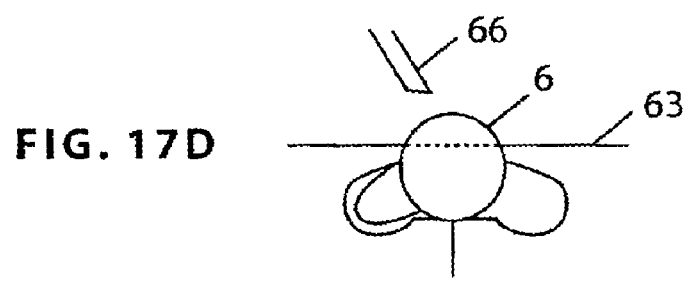
Figure 17E:
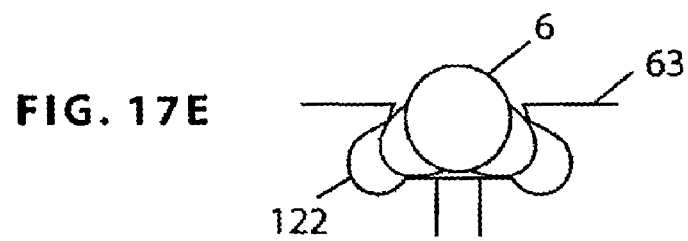
Figure 17F:
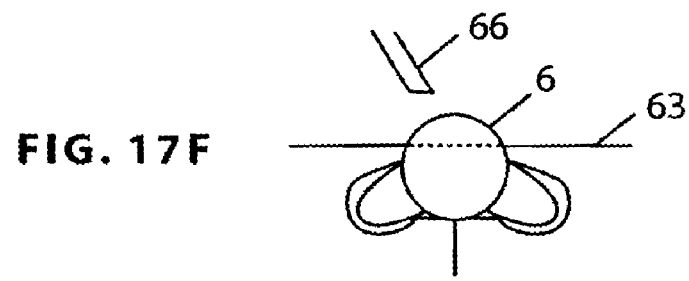

FIG. 17A-F shows the setting of the barbs in vise 63 before and after cutting for a suture having barbs spaced 120 degrees apart. FIG. 17A shows the vise open, suture 6 uncut, with vise notches 120, 122 unused. FIG. 17B shows the vise closed with blade assembly 66 about to cut suture 6. FIG. 17C shows the vise opened after the first set of barbs are cut and placed in notch 122. FIG. 17D shows the vise closed before blade assembly 66 engages suture 6 to cut the second set of barbs. FIG. 17E shows the vise open with two sets of barbs shown and placed in notches 120, 122. FIG. 17F shows the vise closed before blade assembly 66 engages suture element 6 for the cut. After cutting, the suture 6 is removed and examined. As will be apparent to a skilled artisan, additional or fewer notches may be provided for protecting barbs during subsequent cutting steps.

In the twisting method of cutting barbs, suture 6 is set up as previously described and twisted along its axis. The number of twists required is dependant upon the number of barbs, the material of the suture and the diameter of the suture. For example, it has been found that size 0, PDS-2 material requiring 2½" of barbs would require twisting it thirty-nine times for an acceptable result. Of course, too much twisting may cause the suture material to overrun itself, leading to undesirable results including damaged suture material.

Figure 18A:
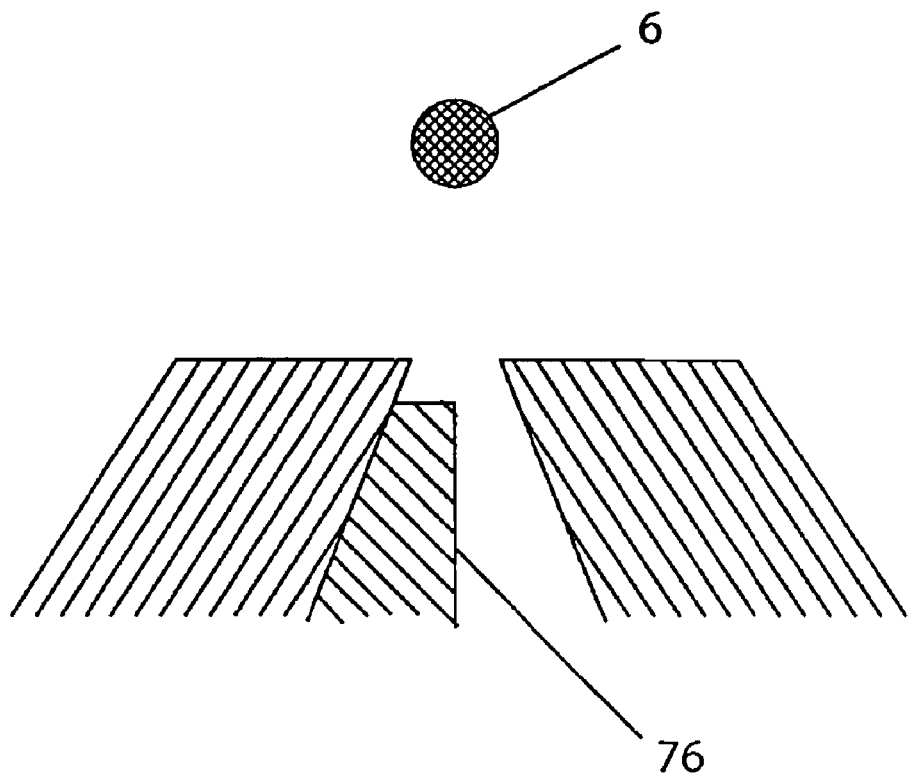
FIGS. 18A-B are front views depicting the setting of the suture in the cutting bed vise before cut using the twisting method of cutting.
Figure 18B:
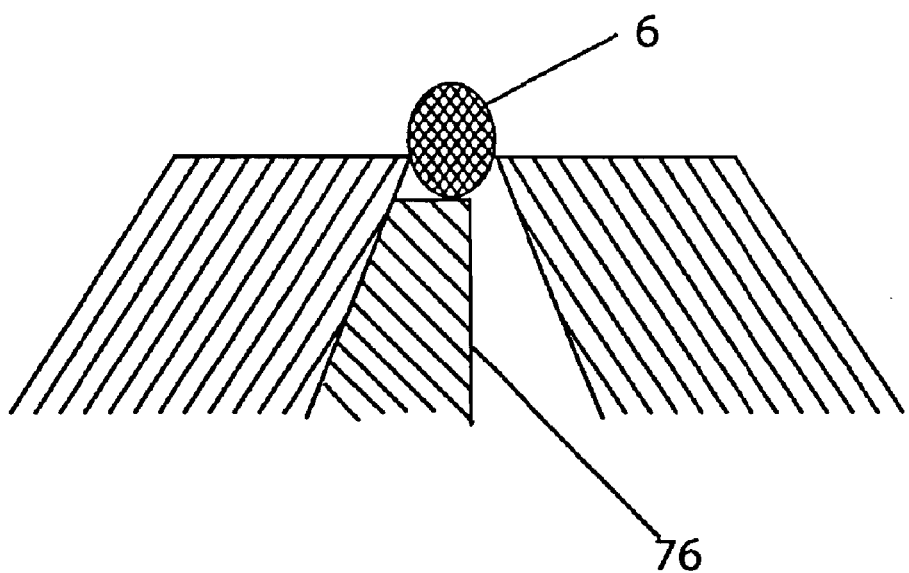

The securing of a twisted suture 6 on cutting bed 56 is, however, slightly different. In this regard, FIGS. 18A and B show the setting of suture 6 in clamp 76 before and during cut. FIG. 18A shows suture 6 being placed in the vise prior to clamping, with FIG. 18B showing the suture post clamping. The lightly clamped suture 6 forms an elliptical shape and is ready to be cut. The cutting method of suture 6 would be the same as that afore-discussed without, however, the need for the suture to be rotated.

Figure 19A:
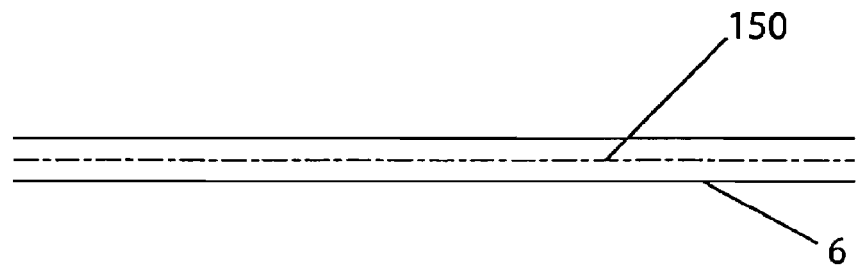
FIGS. 19A-D depict the various conditions of a suture before and after the twisting method of cutting.
Figure 19B:
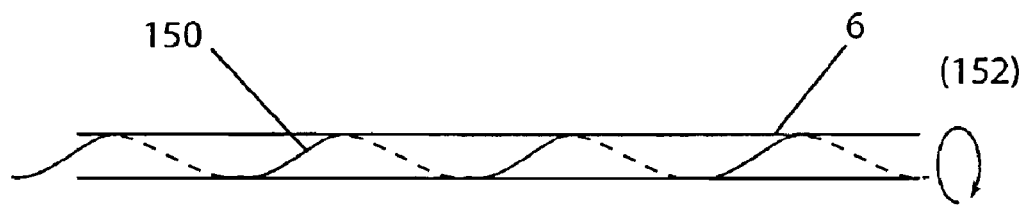
Figure 19C:
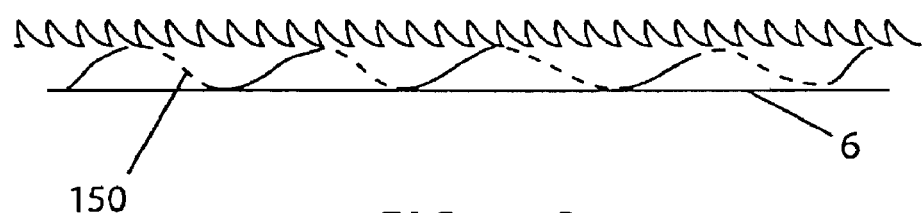

FIGS. 19A-D show the various conditions of suture 6 using the twisting method of cutting. In FIG. 19A the suture 6 is shown unmodified, with an imaginary line 150 shown to depict its longitudinal axis. FIG. 19B shows the suture 6 as it is twisted in direction 152 in preparation for cutting. FIG. 19C shows barbs cut in the twisted condition, with barbs cut along one side thereof. After the suture 6 has been cut and allowed to return to its untwisted condition, the barbs are such as those shown in FIG. 19D where the barbs spiral around the circumference of the suture.

Figure 19D:
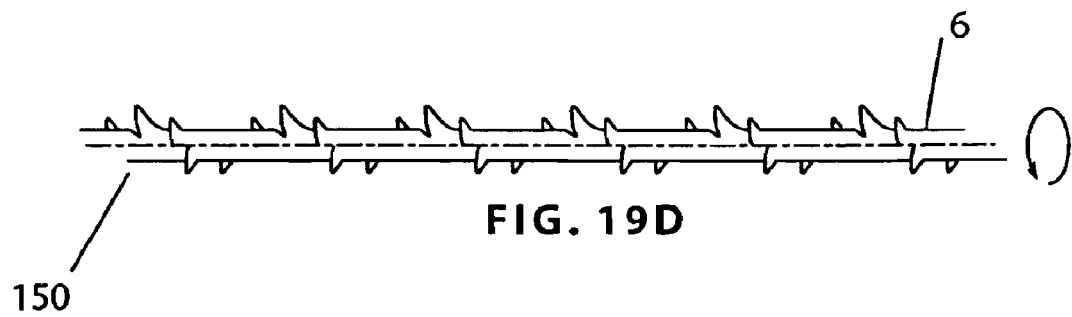
Figure 20:
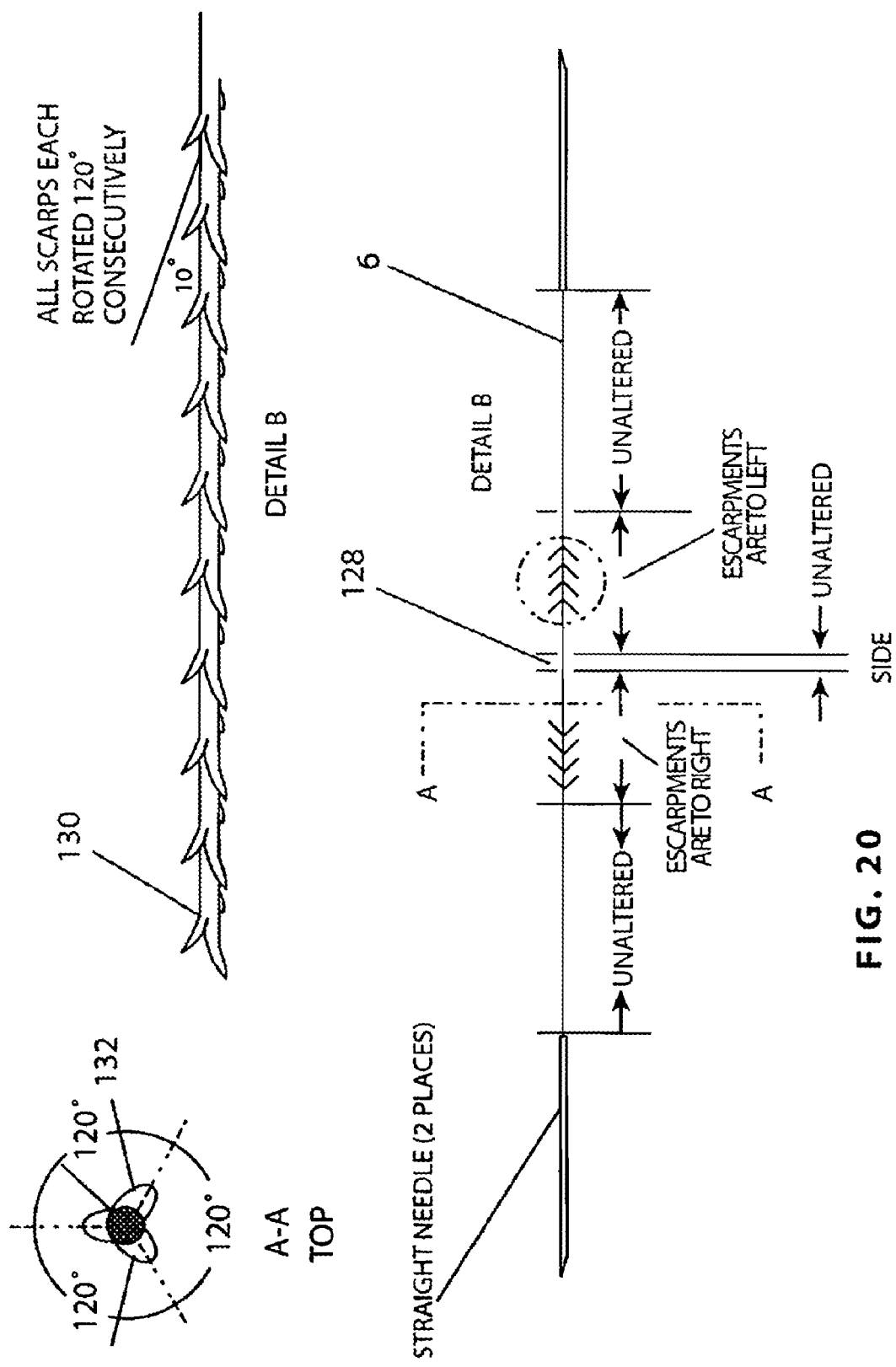
FIG. 20 is a side, top and detail view of a barbed suture using the 120 degree rotation method of cutting.

The difference in the placement of the barbs in the twisted versus the untwisted method can best be seen by comparing FIG. 19D with FIG. 20. In FIG. 20, the suture 6 cut in the untwisted state is shown with spaced barbs at 120° about the circumference of the suture 6. In FIG. 19D, the suture 6 was cut in the twisted state, and, upon de-twisting, the pattern of the barbs takes on a spiral configuration along the length of the suture 6.

Note that by omitting cutting motions when suture 6 is cut in either a twisted or untwisted state, the barbs can be formed in a random configuration on the exterior of the suture. Also, the suture may be cut in both a twisted and untwisted state to produce other types of random configurations of barbs.

Figure 21A:
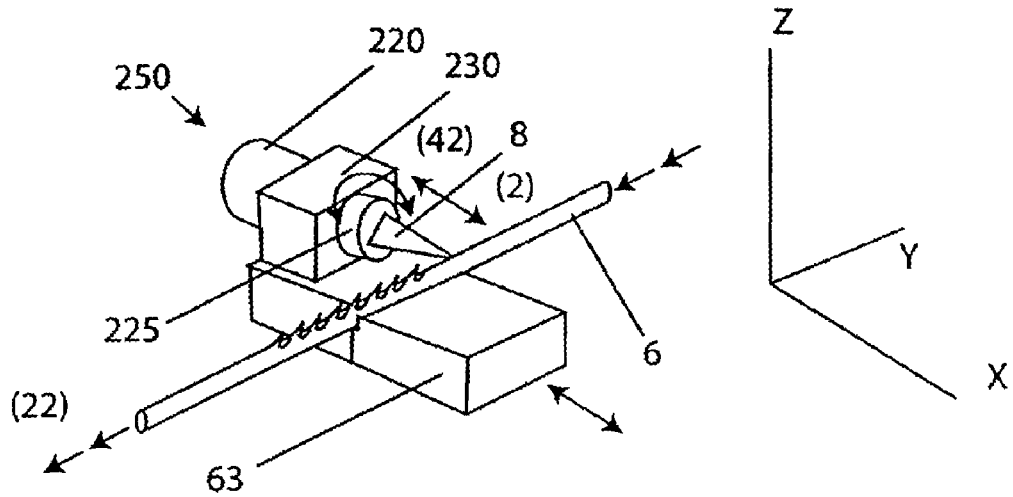
FIGS. 21A-C depict perspective views of a linear indexing mechanism with a rotary reciprocating blade assembly.
Figure 21B:
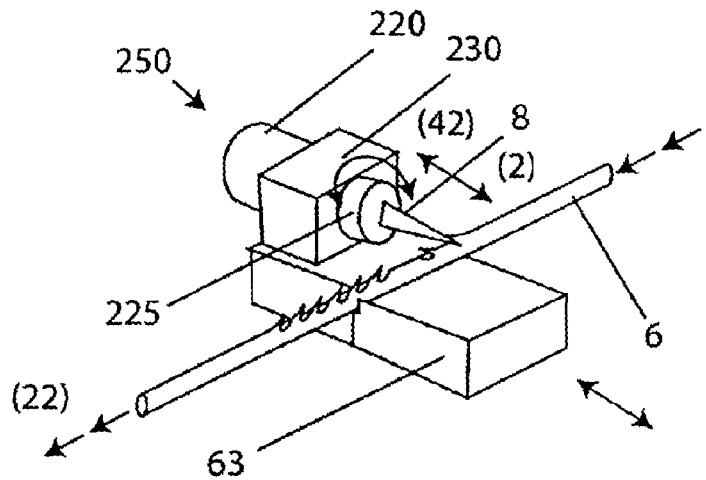
Figure 21C:
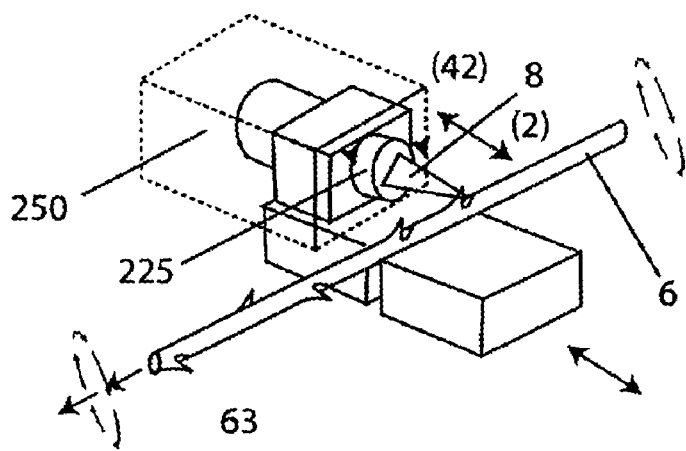
Figure 22:
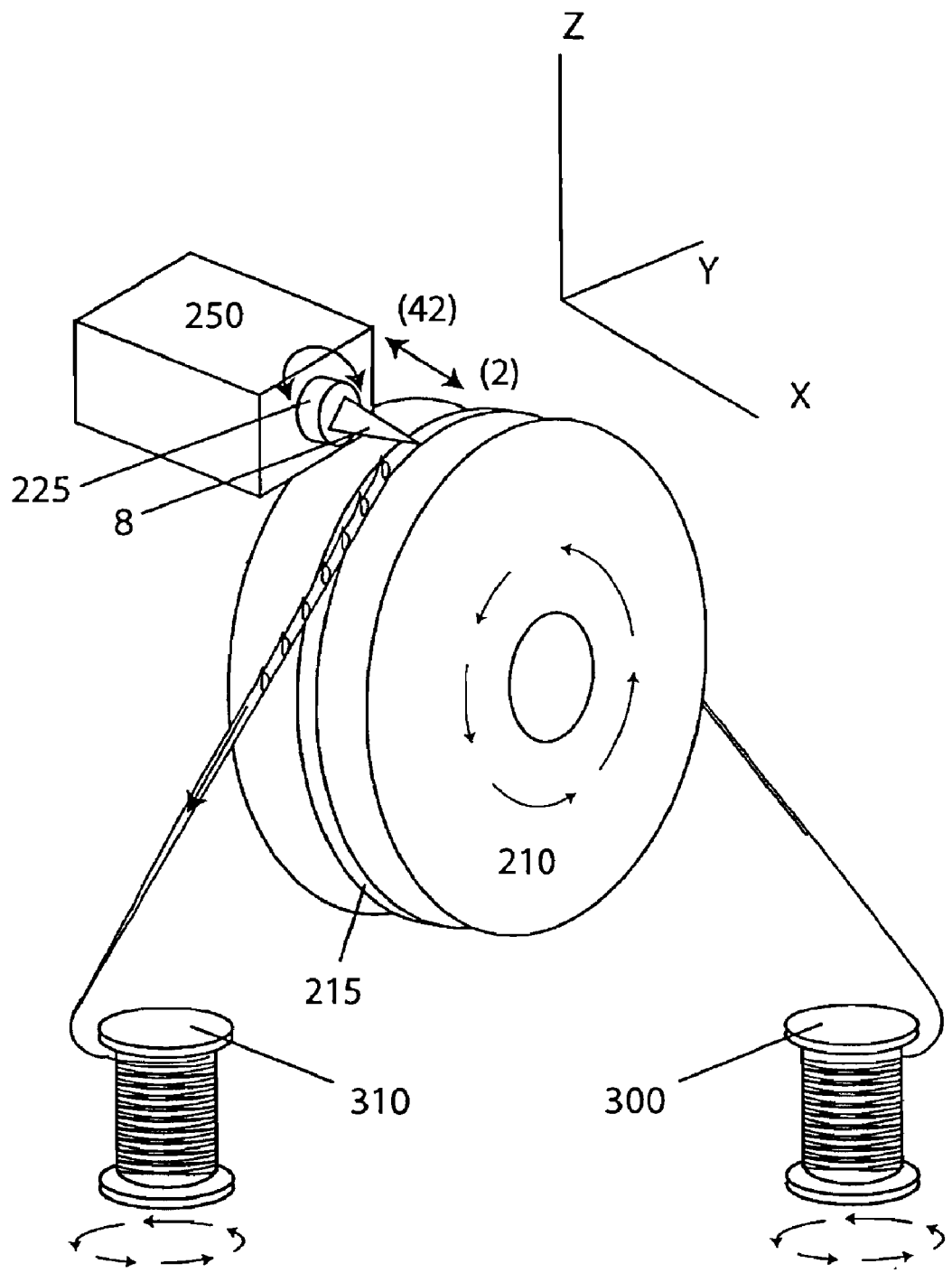
FIG. 22 is a perspective view of a rotational indexing mechanism with a rotary reciprocating blade assembly.

Alternate embodiments for cutting barbs according to the present invention are shown in FIGS. 21-22. FIGS. 21A-C show a linear indexing mechanism for advancing suture 6 along cutting bed vise 63 in direction 22, while reciprocating blade assembly 250 cuts barbs along the axis of suture 6. Suture 6 may be advanced along cutting bed vise 63 in a twisted state to form spiral cut barbs as shown in FIGS. 21A and B, in an untwisted state, or rotated about its axis in increments (e.g. 120 degrees, 180 degrees, etc.) as it advances as shown in FIG. 21C.

Reciprocating blade assembly 250 includes blade 8 connected via arm 225 to a linear reciprocating solenoid 220, which reciprocates in direction 2 and 42 corresponding to the x-axis, and to rotary solenoid 230, which can turn about its axis as shown in FIGS. 21A and B. Cutting bed vise 63 is synchronized with reciprocating blade assembly 250 and the indexing mechanism such that the vise closes to hold suture 6 in place during cutting and opens to allow suture 6 to be advanced by the indexer to the next cutting position.

Linear solenoid 220 and rotary solenoid 230 may be adjusted to control the linear stroke and blade angle of arm 225 of reciprocating blade assembly 250 to allow for varying the depth of the barbs cut in the y and z axes. In addition, rotation of rotary solenoid 230 allows barbs to be cut in the opposite direction along the axis of suture 6 as shown in FIG. 21B. The blade angle and stroke may also be adjusted to sever suture 6 at any desired length.

FIG. 22 shows a rotational indexing mechanism for advancing suture 6. In FIG. 22, suture 6 is shown advancing around a rotating drum 210, while reciprocating blade assembly 250 cuts barbs along the axis of suture 6. Suture 6 is fed onto drum 210 and into cutting channel 215 via suture supply spool 300. Barbed suture is wound off drum 210 onto take-up spool 310. Spools 300 and 310 may supply and take up suture 6 in an untwisted state, or alternatively, either or both spools may be rotated in such a way as to twist and untwist suture 6 to allow spiral cut barbs as described above.

While the invention has been described in connection with what is considered to be the most practical and preferred embodiment, it should be understood that this invention is not to be limited to the disclosed embodiment, but on the contrary, is intended to cover various modifications and equivalent arrangements included within the spirit and scope of the appended claims.

What is claimed is:

1. An apparatus for creating tissue-grasping elements on a suture having a longitudinal axis comprising:
   a cutting bed adapted and configured to support a suture thread at a cutting position;
   a cutting device, the cutting device having a mechanically-constrained path along which the cutting device moves, the mechanically-constrained path selected such that the cutting device passes through a suture supported by the cutting bed at the cutting position to cut a tissue-grasping element having a desired configuration; and
   means for rotating the suture thread between operations of the cutting device whereby the apparatus is adapted to create a plurality of angled cuts of the desired configuration, at a plurality of angularly displaced positions on the suture thread.

2. The apparatus of claim 1, wherein the mechanically-constrained path includes at least two of,
   a transverse x-axis component perpendicular to the longitudinal axis of the suture thread,
   a longitudinal y-axis component parallel to the longitudinal axis of the suture thread, and
   a depth z-axis component perpendicular to the longitudinal axis of the suture thread and the transverse x-axis.

3. The apparatus of claim 1, wherein the mechanically-constrained path includes an oscillating component.

4. The apparatus of claim 1, wherein the cutting device is a single blade.

5. The apparatus of claim 1, wherein the cutting device includes a plurality of blades adapted to create a plurality of tissue-grasping elements of the desired configuration spaced at intervals along the longitudinal axis of the suture.

6. The apparatus of claim 1, wherein the means for rotating the suture thread is also adapted to twist the suture prior to cutting.

7. The apparatus of claim 1, wherein the cutting bed comprises a cutting vise adapted to secure the suture to the cutting bed.

8. The apparatus of claim 1, wherein the cutting bed comprises a channel sized to receive a longitudinal segment of the suture and stabilize the suture during cutting of a tissue-grasping element.

9. The apparatus of claim 1, further comprising a template which constrains the cutting device to move along the mechanically-constrained path.

10. The apparatus of claim 1, further comprising a selectable template which constrains the cutting device to move along a selected mechanically-constrained path.

11. An apparatus for creating angled cuts of a desired configuration on a suture having a longitudinal axis comprising:
   a cutting bed adapted and configured to support a suture thread at a cutting position;
   a cutting device, the cutting device having a preselected path along which the cutting device moves, the preselected path selected such that the cutting device passes through a suture thread supported by the cutting bed at the cutting position to create an angled cut having the desired configuration; and
   a support adapted to hold the suture, which support is rotatable in order to rotate the suture around the longitudinal axis whereby a plurality of tissue-grasping elements having the desired configuration can be created by the cutting device at a plurality of angularly displaced positions on the suture.

12. The apparatus of claim 11, wherein the preselected path includes at least two of:
   a transverse x-axis component perpendicular to the longitudinal axis of the suture thread;
   a longitudinal y-axis component parallel to the longitudinal axis of the suture thread;
   a depth z-axis component perpendicular to the longitudinal axis of the suture thread and the transverse x-axis; and
   an oscillating component.

13. The apparatus of claim 11, wherein the preselected path includes an oscillating component.

14. The apparatus of claim 11, wherein the cutting device is a single blade.

15. The apparatus of claim 11, wherein the cutting device includes a plurality of blades adapted to create a plurality of angled cuts of the desired configuration spaced at intervals along the suture thread.

16. The apparatus of claim 11, wherein the support is also adapted to hold the suture thread in a twisted configuration for cutting.

17. The apparatus of claim 11, wherein the cutting bed comprises a cutting vise adapted to secure the suture thread to the cutting bed during cutting of an angled cut.

18. The apparatus of claim 11, wherein the cutting bed comprises a channel sized to receive a longitudinal segment of the suture thread and stabilize the suture thread during cutting of an angled cut.

19. The apparatus of claim 11, wherein the cutting device is mechanically-constrained to move along the preselected path.

20. An apparatus for creating tissue-grasping elements on a suture thread having a longitudinal axis comprising:

a cutting vise adapted and configured to support a suture thread at a cutting position;

a cutting device, the cutting device having a preselected path along which the cutting device moves, the preselected path selected such that the cutting device passes through a suture supported by the cutting bed at the cutting position to cut a tissue-grasping element having a desired configuration; and a support adapted to hold the suture thread, which support is rotatable in order to rotate the suture thread around the longitudinal axis whereby a plurality of tissue-grasping elements having the desired configuration can be created by the cutting device at a plurality of angularly displaced positions on the suture thread.

\* \* \* \* \*